US011262292B2

(12) United States Patent
Ota et al.

(10) Patent No.: US 11,262,292 B2
(45) Date of Patent: Mar. 1, 2022

(54) FLUID DELIVERY METHOD FOR DELIVERING A LIQUID SAMPLE TO A FLOW CELL AND ANALYSIS DEVICE FOR A LIQUID SAMPLE

(71) Applicant: ARKRAY, Inc., Kyoto (JP)

(72) Inventors: Shinichi Ota, Kyoto (JP); Shigeki Masuda, Kyoto (JP); Shinya Nakajima, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 58 days.

(21) Appl. No.: 16/841,537

(22) Filed: Apr. 6, 2020

(65) Prior Publication Data

US 2020/0319089 A1    Oct. 8, 2020

(30) Foreign Application Priority Data

Apr. 8, 2019    (JP) .............................. JP2019-073451

(51) Int. Cl.
*G01N 21/05*    (2006.01)
*G01N 33/493*    (2006.01)
(Continued)

(52) U.S. Cl.
CPC ........ *G01N 21/05* (2013.01); *B01L 3/502776* (2013.01); *G01N 15/1484* (2013.01);
(Continued)

(58) Field of Classification Search
CPC .. G01N 21/05; G01N 33/493; G01N 33/4915; G01N 15/147; G01N 2015/1413;
(Continued)

(56) References Cited

U.S. PATENT DOCUMENTS 5,690,895 A * 11/1997 Matsumoto ........ G01N 15/1404
356/246
7,434,982 B2 * 10/2008 Nagasawa ............. B01F 5/0453
366/147
(Continued)

FOREIGN PATENT DOCUMENTS

JP    2018-112516 A    7/2018
JP    2019-007893 A    1/2019

OTHER PUBLICATIONS

The extended European search report issued by the European Patent Office dated Aug. 4, 2020, which corresponds to European Patent Application No. 20168549.2-1020 and is related to U.S. Appl. No. 16/841,537.

*Primary Examiner* — Michael P LaPage
(74) *Attorney, Agent, or Firm* — Studebaker & Brackett PC

(57) ABSTRACT

A fluid delivery method for delivering a liquid sample to a flow cell including a taper section including a first and a second inner walls opposing the first inner wall, which is inclined to the second inner wall so that a distance between the first and the second inner walls at a downstream side of the taper section is shorter than a distance at an upstream side of the taper section, and including measurement flow path provided downstream of the taper section, through which a liquid sample flows together with a sheath fluid. The fluid delivery method includes sample introduction of delivering the liquid sample into the taper section along the second inner wall until the liquid sample reaches the measurement flow path, and sample pressing by delivering the sheath fluid into the taper section along the first inner wall after the liquid sample reaches the measurement flow path.

8 Claims, 15 Drawing Sheets

(51) Int. Cl.
   *B01L 3/00* (2006.01)
   *G01N 15/14* (2006.01)
   *G01N 33/49* (2006.01)
   *B01L 9/00* (2006.01)

(52) U.S. Cl.
   CPC ............ *G01N 33/493* (2013.01); *B01L 9/527* (2013.01); *G01N 33/4915* (2013.01); *G01N 2015/1413* (2013.01)

(58) Field of Classification Search
   CPC ....... G01N 2015/1006; G01N 15/1484; G01N 2015/1493; G01N 2015/1497; G01N 2015/1486; G01N 2015/1409; G01N 15/1404; G01N 21/11; G01N 2021/058; G01N 35/1011; G01N 35/04; G01N 2035/0474; B01L 2300/0816; B01L 9/527; B01L 2300/0861; B01L 2400/0487; B01L 3/502776
   See application file for complete search history.

(56) References Cited

U.S. PATENT DOCUMENTS

| | | | |
|---|---|---|---|
| 8,487,273 B2 * | 7/2013 | Ito | B01L 3/502776 250/458.1 |
| 9,409,172 B2 * | 8/2016 | Shinoda | B01L 3/502761 |
| 2003/0129090 A1 | 7/2003 | Farrell | |
| 2005/0123450 A1 * | 6/2005 | Gilbert | G01N 15/1484 422/81 |
| 2008/0311005 A1 * | 12/2008 | Kim | G01N 15/1404 422/82.05 |
| 2011/0271746 A1 * | 11/2011 | Shinoda | B01L 3/0268 73/61.71 |
| 2011/0284378 A1 * | 11/2011 | Shinoda | G01N 27/44791 204/603 |
| 2014/0158212 A1 * | 6/2014 | Vrane | G01N 15/1404 137/12 |
| 2018/0372612 A1 | 12/2018 | Masuda | |
| 2019/0366343 A1 * | 12/2019 | Takahashi | B01L 3/502776 |

\* cited by examiner

FLUID DELIVERY METHOD FOR DELIVERING A LIQUID SAMPLE TO A FLOW CELL AND ANALYSIS DEVICE FOR A LIQUID SAMPLE

CROSS-REFERENCE TO RELATED APPLICATION

This application claims priority under 35 USC 119 from Japanese Patent Applications No. 2019-073451, filed on Apr. 8, 2019 and No. 2020-051915, filed on Mar. 23, 2020, the disclosures of which are incorporated by reference herein.

BACKGROUND

Technical Field

The present disclosure relates to a fluid delivery method for delivering a liquid sample to a flow cell, and to an analysis device utilizing this method.

Related Art

Japanese Patent Application Laid-Open (JP-A) Nos. 2018-112516 and 2019-7893 disclose flow cells that are equipped with a sheath fluid flow path into which a sheath fluid flows, a sample flow path into which a liquid sample flows, and a confluent flow path where the sheath fluid flow path and the sample flow path join together and where formed elements contained in the liquid sample is imaged.

An aim of the technology described in JP-A No. 2019-7893 is, in the confluent flow path, to cause the sheath fluid flowing from the sheath fluid flow path to press the liquid sample flowing from the sample flow path onto a bottom face of a flow cell to a flattened shape in order to image the formed elements in the liquid sample with an imaging device facing toward the bottom face of the flow cell. However, since the liquid sample sometimes does not become a pressed state onto the bottom face, sheath fluid is interposed between the liquid sample and the imaging device, resulting in making it difficult to clearly image the formed elements.

SUMMARY

A fluid delivery method of the present disclosure is a fluid delivery method for delivering a liquid sample to a flow cell including a taper section that includes a first inner wall and a second inner wall opposing the first inner wall, the first inner wall being inclined to the second inner wall so that a distance between the first inner wall and the second inner wall at a downstream side of the taper section is shorter than a distance between the first inner wall and the second inner wall at an upstream side of the taper section, the flow cell including a measurement flow path provided at downstream of the taper section, the liquid sample flowing through the taper section together with a sheath fluid. The fluid delivery method includes sample introduction by delivering the liquid sample into the taper section along the second inner wall opposing the taper face until the liquid sample reaches the measurement flow path; and sample pressing by delivering the sheath fluid into the taper section along the first inner wall after the liquid sample reaches the measurement flow path.

An analysis device of the present disclosure is an analysis device including a flow cell, a sheath fluid delivery device, a sample delivery device, a measurement device, and a controller. The flow cell includes a taper section that includes a first inner wall and a second inner wall opposing the first inner wall, the first inner wall being inclined to the second inner wall so that a distance between the first inner wall and the second inner wall at a downstream side of the taper section is shorter than a distance between the first inner wall and the second inner wall at an upstream side of the taper section, the flow cell including a measurement flow path provided at downstream of the taper section, and the liquid sample flowing through the taper section together with a sheath fluid. The sheath fluid delivery device is configured to deliver the sheath fluid along the first inner wall. The sample delivery device is configured to deliver the liquid sample along an inner wall opposing the first inner wall. The measurement device is configured to measure the liquid sample flowing in the measurement flow path. The controller is configured to control the sample delivery device so as to deliver the liquid sample along the second inner wall until the liquid sample reaches the measurement flow path, and to control the sheath fluid delivery device so as to deliver the sheath fluid along the first inner wall after the liquid sample reaches the measurement flow path.

An aspect of the present disclosure makes it possible, in a flow cell that causes a liquid sample to flow therein while a sheath fluid presses the liquid sample onto an inner wall of the flow cell, for the liquid sample to certainly flow in contact with the inner wall at an imaging position.

BRIEF DESCRIPTION OF THE DRAWINGS

Exemplary embodiments will be described in detail based on the following figures, wherein.

DETAILED DESCRIPTION

Figure 1:
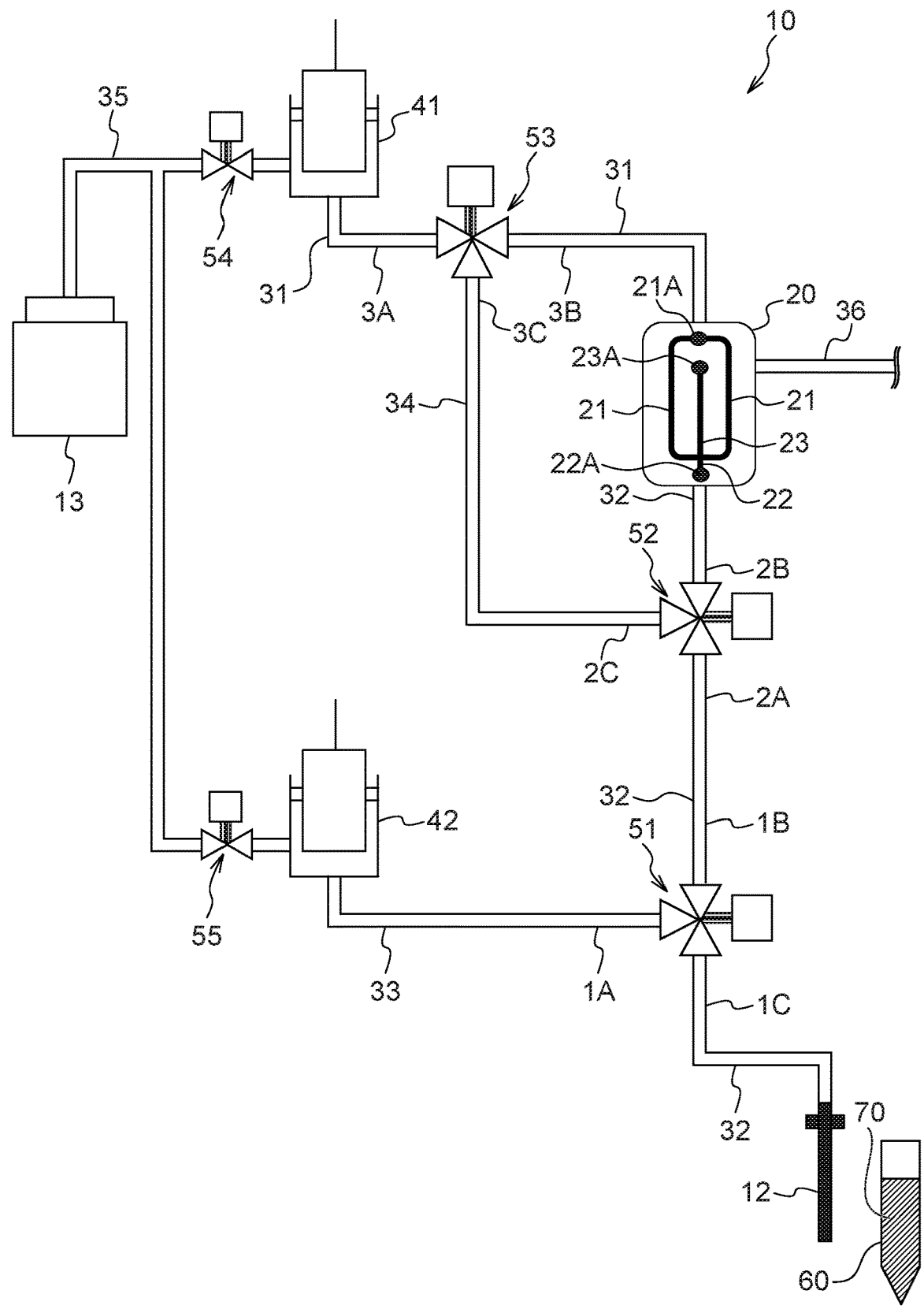
FIG. 1 is a schematic diagram of an analysis device of an exemplary embodiment of the present disclosure.

An exemplary embodiment of the present disclosure is as described below. Note that reference numerals appended to each configuration element in the following description corresponds to reference numerals shown in the drawings for the convenience of reference. However, the present disclosure is obviously not limited thereby. Moreover, in the present disclosure, a side of each of the flow paths nearest to a liquid inflow source is referred to as being "upstream", and a side nearest to an outflow destination of a liquid is referred to as being "downstream".

Fluid Delivery Method for Liquid Sample 70

First Aspect

A first aspect of the present disclosure is a fluid delivery method to deliver a liquid sample 70 to a flow cell 20 including a confluent flow path 23 through which the liquid sample 70 and a sheath fluid 80 flow, a sample flow path 22 that introduces the liquid sample 70 into the confluent flow path 23, and at least one sheath fluid flow path 21 that introduces the sheath fluid 80 into the confluent flow path 23. The confluent flow path 23 includes a confluent section 23B where the sample flow path 22 and the sheath fluid flow path 21 join together, a flat section 23D that is disposed at the downstream side of the confluent section 23B, that is formed along one of opposing wall faces of the confluent section 23B, and that has a shorter distance between the opposing wall faces than that in the confluent section 23B, a taper section 23C that interconnects the confluent section 23B and the flat section 23D and in which a distance between the opposing wall faces gradually becomes shorter on progression downstream. The sheath fluid flow path 21 introduces the sheath fluid 80 into the confluent section 23B along a wall face provided with a first inner wall 23E in the taper section 23C. The sample flow path 22 introduces the liquid sample 70 into the confluent section 23B along a wall face opposing the wall face provided with the first inner wall 23E.

In other words, the flow cell 20 employed in the liquid sample 70 fluid delivery method of the present aspect includes the sheath fluid flow path 21, the sample flow path 22, and the confluent flow path 23. The confluent flow path 23 of the flow cell 20 includes, from the upstream side, the confluent section 23B, the taper section 23C, and the flat section 23D. The taper section 23C includes the first inner wall 23E and a second inner wall 23F opposing the first inner wall 23E. The first inner wall 23E is inclined in a direction so as to approach the second inner wall 23F on progression from upstream to downstream. A distance between the first inner wall 23E and the second inner wall 23F at a downstream side of the taper section is shorter than a distance between the first inner wall 23E and the second inner wall 23F at an upstream side of the taper section. Then, in the confluent section 23B of the confluent flow path 23 in the flow cell 20, the sheath fluid 80 is introduced into the confluent section 23B from the side of the wall face provided with the first inner wall 23E. Thus, a force to press the liquid sample 70, described later, against the wall face opposing the first inner wall 23E is generated by the sheath fluid 80 flowing from upstream to downstream along the first inner wall 23E. Thereby, the liquid sample 70 introduced into the confluent section 23B is pressed by the sheath fluid 80 onto the wall face opposing the wall face provided with the first inner wall 23E, namely, onto the wall face on the side the liquid sample 70 is pressed by the sheath fluid 80 flowing along the first inner wall 23E.

In order for the fluid delivery pressure of the liquid sample 70 in the confluent flow path 23 along the inner wall opposing the first inner wall 23E until the liquid sample 70 reaches the flat section 23D serving as a measurement flow path, to be higher than the fluid delivery pressure of the sheath fluid 80 in the confluent flow path 23, the liquid sample 70 analysis method of the present aspect includes sample introduction by delivering the liquid sample 70 into the taper section 23C, and sample pressing by delivering the sheath fluid 80 into the taper section 23C along the first inner wall 23E after the liquid sample 70 reaches the flat section 23D serving as the measurement flow path.

Namely, until the liquid sample 70 reaches the flat section 23D serving as the measurement flow path, as the sample introduction, the liquid sample 70 is delivered into the sample flow path 22 and the sheath fluid 80 is delivered into the sheath fluid flow path 21 so that the fluid delivery pressure of the liquid sample 70 in the confluent flow path 23 is higher than the fluid delivery pressure of the sheath fluid 80 in the confluent flow path 23. If the fluid delivery pressure of the liquid sample 70 in the confluent flow path 23 (i.e. the confluent section 23B, the flat section 23D, and the taper section 23C) until the liquid sample 70 reaches the flat section 23D, namely in the confluent flow path 23 where both the liquid sample 70 and the sheath fluid 80 flow, were lower than the fluid delivery pressure of the sheath fluid 80, the liquid sample 70 would flow in a central portion of laminar flow of the sheath fluid 80 where the fluid delivery pressure is comparatively low. Then, the liquid sample 70 would accordingly flow with a separation from the wall face opposing the wall face provided with the first inner wall 23E, namely with a separation from the wall face on the side the liquid sample 70 is attempting to be pressed against by the sheath fluid 80 flowing along the first inner wall 23E. In order to address this issue, until the liquid sample 70 reaches the flat section 23D, the fluid delivery pressure of the liquid sample 70 in the confluent flow path 23 is made higher than the fluid delivery pressure of the sheath fluid 80. The liquid sample 70 is accordingly not affected by the delivery flow of the sheath fluid 80, and is accordingly able to reach the flat section 23D by flowing along the wall face opposing the wall face provided with the first inner wall 23E.

Then, after the liquid sample 70 reaches the flat section 23D, as the sample pressing, the liquid sample 70 is delivered into the sample flow path 22 and the sheath fluid 80 is delivered into the sheath fluid flow path 21 so that the fluid delivery pressure of the liquid sample 70 in the confluent flow path 23 is lower than the fluid delivery pressure of the sheath fluid 80 in the confluent flow path 23. Namely, the fluid delivery pressure of the liquid sample 70 in the confluent flow path 23 (the confluent section 23B, the flat section 23D, and the taper section 23C) where the liquid sample 70 and the sheath fluid 80 both flow is made lower than the fluid delivery pressure of the sheath fluid 80 flowing in the confluent flow path 23. Thus, the liquid sample 70 is delivered up to the flat section 23D by flowing along the wall face 23Y (the second inner wall 23F) opposing the wall face 23X provided with the first inner wall 23E, while being pressed against this wall face 23Y by the fluid delivery pressure sheath fluid 80 of higher fluid delivery pressure. Then, the fluid delivery pressure of the liquid sample 70 inside the confluent flow path 23 is lower than the fluid delivery pressure of the sheath fluid 80 inside the confluent flow path 23. Thus, although the liquid sample 70 tends to flow with a separation from the wall face 23Y opposing the wall face 23X provided with the first inner wall 23E, the liquid sample 70 actually flows along the one wall face from out of the opposing wall faces due to being pressed by the sheath fluid 80 having the higher fluid delivery pressure inside the confluent flow path 23. Moreover, the liquid sample 70 is spread out into a flattened planar shape so as to have a thickness that gets thinner on progression along the wall face opposing the wall face provided with the first inner wall 23E. This thereby facilitates measurement and observation of the liquid sample 70 in the flat section 23D. The transition to the sample pressing described above may be performed at any freely selected point in time as long as this is after performing the sample introduction.

In the sample introduction, it is sufficient for the liquid sample 70 and the sheath fluid 80 to flow in the flat section 23D in a state in which the fluid delivery pressure of the liquid sample 70 in the confluent flow path 23 is higher than the fluid delivery pressure of the sheath fluid 80 in the confluent flow path 23. For example, in a case in which the liquid sample 70 has already reached the flat section 23D but the fluid delivery pressure of the liquid sample 70 flowing in the confluent flow path 23 is lower than the fluid delivery pressure of the sheath fluid 80, the fluid delivery pressure of the liquid sample 70 may be raised so that the liquid sample 70 flows to the flat section 23D, and then after the liquid sample 70 delivered with raised fluid delivery pressure reaches the flat section 23D, the fluid delivery pressure of the liquid sample 70 may be made lower than the fluid delivery pressure of the sheath fluid 80.

Note that the fluid delivery pressure of the liquid sample 70 and the fluid delivery pressure of the sheath fluid 80 in the confluent flow path 23 can be controlled with a freely chosen method. For example, a pressure sensor or the like may be provided in the confluent flow path 23, the fluid delivery pressure inside the confluent flow path 23 is measured thereby, and the output of a device (a pump, for example) employed to cause the sheath fluid 80 or the liquid sample 70 to flow into the sheath fluid flow path 21 or the sample flow path 22 may be adjusted based on the measurement results thereof. Alternatively, the actual fluid delivery pressure in the sheath fluid flow path 21 and the sample flow path 22 may be measured using a pressure sensor or the like, and the fluid delivery pressures in the confluent flow path 23 computed and controlled from the ratios of the cross-sectional areas of the flow paths of the sheath fluid flow path 21 and the sample flow path 22 to the cross-sectional area of the confluent flow path 23. Moreover, control of the fluid delivery pressure may be achieved by providing a controller in an inflow device such as a pump or the like to measure the fluid delivery pressure of the confluent flow path 23 and the sheath fluid flow path 21 and the sample flow path 22 etc., and then controlling the output of the inflow device based on the measurement results.

As described above, the liquid sample 70 is spread out by the sample pressing into a flattened planar shape so as to have a thickness that gets thinner on progression along the wall face opposing the wall face provided with the first inner wall 23E. Then, a measurement of the liquid sample 70 flowing through the flat section 23D may be executed after the sample pressing. There are no particular limitations to the measurement device 11 employed to measure the liquid sample 70, and any appropriate unit may be employed therefor according to the measurement item. For example, an optical unit such as a spectrophotometer and a camera to image images may be employed therefor, or an electronic unit such as a sensor may be employed therefor. Measurement of the liquid sample 70 includes observation and imaging of images imaged by a camera or the like.

The measurement device 11 is preferably provided at a position appropriate for measurement of the liquid sample 70 spread out into a flattened planar shape. More specifically, the liquid sample 70 is spread out into a flattened planar shape as it flows from the taper section 23C into the flat section 23D. Accordingly, the measurement device 11 is suitably provided at a position facing toward the flat section 23D and the taper section 23C, and is suitably provided at a position facing toward a position from the taper section 23C across to the flat section 23D. The liquid sample 70 is spread out into the flattest planar shape at the position facing toward positions spanning from the taper section 23C across the flat section 23D. Accordingly, the measurement device 11 is preferably provided at a position facing toward a position spanning from the taper section 23C across to the flat section 23D, in other words, at a position facing an upstream section of the flat section 23D. Moreover, since the liquid sample 70 flows along the wall face 23Y opposing the wall face 23X provided with the first inner wall 23E, the measurement device 11 is preferably provided at a position facing the liquid sample 70 across this wall face 23Y. Thereby, the sheath fluid 80 is not interposed between the measurement device 11 and the liquid sample 70, and the liquid sample 70 can be measured with the measurement device 11 without being affected by the sheath fluid 80. Note that flow path through which the liquid sample 70 flows for measurement by the measurement device 11 is the flow path connected to the downstream end of the taper section 23C and corresponds to the measurement flow path. For example, in a case in which the measurement device 11 is provided at a position facing toward the upstream section of the flat section 23D, then the flat section 23D is the measurement flow path. Moreover, for example, in a case in which the measurement device 11 is provided at a position facing toward an intermediate section between the upstream section and the downstream section of the taper section 23C, then this intermediate section is the measurement flow path.

A determination of, after measuring a fluid delivery pressure of the liquid sample 70 in a flow path, whether or not the indicated fluid delivery pressure is within a particular range may be performed prior to the measurement of the liquid sample 70 described above. The fluid delivery pressure is not stable immediately after transition to the liquid sample 70 pressing in a case in which there is a difference between the fluid delivery pressure for introducing the liquid sample 70 into the confluent flow path 23 in the sample introduction and the fluid delivery pressure for introducing the liquid sample 70 into the confluent flow path 23 in the sample pressing. For example, in the sample introduction, in order to achieve quick introduction of the liquid sample 70 into the sample flow path 22 and the flow path of the flow cell 20, sometimes the liquid sample 70 is delivered at a higher fluid delivery pressure than the fluid delivery pressure when the liquid sample 70 is introduced at the sample pressing. Namely, the fluid delivery pressure of the liquid sample 70 into the confluent flow path 23 at the sample introduction is sometimes greater than the fluid delivery pressure of the liquid sample 70 into the confluent flow path 23 at the sample pressing. In such circumstances, the fluid delivery pressure of the liquid sample 70 in the confluent flow path 23 is not stable immediately after transition from the sample introduction to the sample pressing, and is sometimes higher than the fluid delivery pressure when the liquid sample 70 is being introduced in the sample pressing. Measurement precision would accordingly deteriorate the measurement of the liquid sample 70 to be executed in this state. Therefore, in order to address this issue, the fluid delivery pressure of the liquid sample 70 in the confluent flow path 23 is measured over a fixed period of time, and transition is made to the measurement of the liquid sample 70 when the fluid delivery pressure is within a particular fluid delivery pressure range. On the other hand, when the fluid delivery pressure is not within the particular pressure range, then delivery of the sheath fluid 80 and the liquid sample 70 is made for the fixed period of time, and then after the fluid delivery pressure of the liquid sample 70 in the confluent flow path 23 is measured again after the fixed period of time, determination is made as to whether or not to transition to the measurement of the liquid sample 70. This thereby enables measurement precision deterioration to be avoided even in a case in which the fluid delivery pressure of the liquid sample 70 in the confluent flow path 23 at the sample introduction is greater than the fluid delivery pressure of the liquid sample 70 in the confluent flow path 23 at the sample pressing. Furthermore, the liquid sample 70 can be quickly introduced into the sample flow path 22 and the flow path of the flow cell 20 in the sample introduction.

Moreover, whether or not the liquid sample 70 reaches the flat section 23D may be determined by whether or not a particular attribute of the liquid sample 70 (for example, a color of liquid or a particular component) is detected using the measurement device 11 installed at the flat section 23D. Alternatively, a sensor capable of detecting the liquid sample 70 may be provided in the flat section 23D, and determination may be made based on response of the sensor.

Second Aspect

A second aspect of the fluid delivery method to deliver a liquid sample 70 of the present disclosure also employs a flow cell 20 equipped with flow paths having similar configuration to those of the first aspect.

However, the fluid delivery method to deliver the liquid sample 70 of the present aspect includes, after the sheath fluid 80 fills the confluent flow path 23, the sample introduction and the sample pressing of the first aspect, wherein delivery of the sheath fluid 80 to the sheath fluid flow path 21 is halted in the sample introduction. Namely, in a state in which the sheath fluid 80 is delivered into the sheath fluid flow path 21, and the confluent flow path 23 (the confluent section 23B, the flat section 23D, and the taper section 23C) is filled with the sheath fluid 80, delivery of the sheath fluid 80 to the sheath fluid flow path 21 is halted. In the state in which delivery of the sheath fluid 80 into the sheath fluid flow path 21 is halted, as the sample introduction, the liquid sample 70 is delivered into the sample flow path 22 until the liquid sample 70 reaches the flat section 23D. Then, after the liquid sample 70 reaches the flat section 23D, namely in the sample pressing, the liquid sample 70 is delivered into the sample flow path 22 and the sheath fluid 80 is delivered into the sheath fluid flow path 21 so that the fluid delivery pressure of the liquid sample 70 in the confluent flow path 23 is lower than the fluid delivery pressure of the sheath fluid 80 in the confluent flow path 23.

Namely, the fluid delivery pressure of the sheath fluid 80 in the confluent flow path 23 is substantially nil, or extremely low, in the sample introduction.

Then in this state, the liquid sample 70 is then caused to flow into the sample flow path 22 until the liquid sample 70 reaches the flat section 23D. Note that, since the fluid delivery pressure of the sheath fluid 80 in the confluent flow path 23 is nil or extremely low as described above, the fluid delivery pressure of the liquid sample 70 in the confluent flow path 23 is obviously higher than the fluid delivery pressure of the sheath fluid 80 in the confluent flow path 23.

Then, after the liquid sample 70 reaches the flat section 23D, the liquid sample 70 and the sheath fluid 80 are delivered in a similar manner to in the sample pressing of the first aspect, thereby enabling observation of the liquid sample 70 to be facilitated.

Other configuration is similar to in the first aspect.

Analysis Device 10 for Liquid Sample 70

An aspect of an analysis device 10 for a liquid sample 70 of the present disclosure employs a flow cell 20 including a confluent flow path 23 through which the liquid sample 70 and a sheath fluid 80 flow, a liquid sample flow path 22 that introduces the liquid sample 70 into the confluent flow path 23, and at least one sheath fluid flow path 21 that introduces the sheath fluid 80 into the confluent flow path 23. The confluent flow path 23 includes a confluent section 23B where the sample flow path 22 and the sheath fluid flow path 21 join together, a flat section 23D that is disposed at the downstream side of the confluent section 23B, that is formed along one of opposing wall faces of the confluent section 23B, and that has a shorter distance between the opposing wall faces than that in the confluent section 23B, and a taper section 23C that interconnects the confluent section 23B and the flat section 23D and in which a distance between opposing wall faces gradually becomes shorter on progression downstream. The sheath fluid flow path 21 introduces the sheath fluid 80 into the confluent section 23B from the other wall face side out of the opposing wall faces.

Namely, the significance and configuration of the flow cell 20 of the present aspect are similar to those of the liquid sample 70 fluid delivery method described above.

Moreover, the analysis device 10 for the liquid sample 70 of the present aspect includes the measurement device 11 installed at a position facing toward the flat section 23D, a first flow path 31 connected at the upstream of the sheath fluid flow path 21, a first pump 41 to supply the sheath fluid 80 to the flow cell 20 through the first flow path 31, a second flow path 32 connected at the upstream of the sample flow path 22, a second pump 42 to supply the liquid sample 70 to the flow cell 20 through the second flow path 32, and a controller 100 to control the first pump 41 and the second pump 42.

Moreover, in the analysis device 10 for the liquid sample 70 of the present aspect, the controller 100 controls the first pump 41 and the second pump 42 so that, until the liquid sample 70 reaches the flat section 23D, the fluid delivery pressure of the liquid sample 70 in the confluent flow path 23 is higher than the fluid delivery pressure of the sheath fluid 80 in the confluent flow path 23.

For example, until the liquid sample 70 reaches the flat section 23D, the controller 100 controls the first pump 41 and the second pump 42 so that the fluid delivery pressure of the liquid sample 70 in the confluent flow path 23 is higher than the fluid delivery pressure of the sheath fluid 80 in the confluent flow path 23, and the liquid sample 70 is delivered into the sample flow path 22 and the sheath fluid 80 is delivered into the sheath fluid flow path 21. Namely, the pressure with which the second pump 42 delivers the liquid sample 70 into the confluent flow path 23 is made higher than the pressure with which the first pump 41 delivers the sheath fluid 80 into the confluent flow path 23. The technical significance of adopting such control to introduce the liquid sample 70 and the sheath fluid 80 into the flow cell 20 is the same as that of the first aspect described above, and so detailed explanation thereof will be omitted.

Then, after the liquid sample 70 reaches the flat section 23D, namely in a state in which the liquid sample 70 reaches the flat section 23D, the controller 100 controls the first pump 41 and the second pump 42 so that the fluid delivery pressure of the liquid sample 70 in the confluent flow path 23 is lower than the fluid delivery pressure of the sheath fluid 80 in the confluent flow path 23, and the liquid sample 70 is delivered into the sample flow path 22 and the sheath fluid 80 is delivered into the sheath fluid flow path 21. Namely, the pressure with which the second pump 42 delivers the liquid sample 70 into the confluent flow path 23 is made lower than the pressure with which the first pump 41 delivers the sheath fluid 80 into the confluent flow path 23. The technical significance of adopting such control when introducing the liquid sample 70 and the sheath fluid 80 into the flow cell 20 is the same as that of the first aspect described above, and so detailed explanation thereof will be omitted.

The fluid delivery pressure of the liquid sample 70 in the confluent flow path 23 and the fluid delivery pressure of the sheath fluid 80 therein may be controlled by any freely chosen means. The means of control are the same as in the first aspect described above, and so detailed explanation thereof will be omitted.

Moreover, the technical significance of making the fluid delivery pressure of the liquid sample 70 in the confluent flow path 23 in the sample introduction greater than the fluid delivery pressure of the liquid sample 70 in the confluent flow path 23 in the sample pressing, is the same as that of the first aspect described above, and so detailed explanation thereof will be omitted.

Moreover, the means to determine whether or not the liquid sample 70 reaches the flat section 23D are the same as in the first aspect described above, and so detailed explanation thereof will be omitted.

Note that, in the present aspect, the "opposing wall faces" refers to the top face 23X and the bottom face 23Y of the confluent flow path 23, and the liquid sample 70 is pressed by the sheath fluid 80 from above onto the bottom face 23Y that is the "wall face opposing the wall face provided with the first inner wall 23E". However, the liquid sample 70 analysis method of the present disclosure and the liquid sample 70 analysis device 10 of the present disclosure are not limited to such an aspect. For example, the "wall face opposing the wall face provided with the first inner wall 23E" may be set to be the face on the upper side of the confluent flow path 23, and the liquid sample 70 may be pressed by the sheath fluid 80 from below against this upper face. Alternatively, a configuration may be adopted in which the "opposing wall faces" is set as right and left wall faces opposing each other, with one of the right and left wall faces, for example the left wall face, employed as the "wall face opposing the wall face provided with the first inner wall 23E", so that the liquid sample 70 is pressed onto the face on the left side by the sheath fluid 80 flowing from the right side.

Exemplary Embodiments

Explanation follows regarding an exemplary embodiment of the present disclosure, with reference to the drawings.

FIG. 1 schematically illustrates an exemplary embodiment of the liquid sample 70 analysis device 10. In the present exemplary embodiment, a first flow path 31 and a second flow path 32 are connected to a flow cell 20 as inflow paths. A waste liquid path 36 is also connected as an outflow path from the flow cell 20.

Configuration of Analysis Device 10

The sheath fluid 80 (see FIG. 13) is supplied from the first pump 41 into the sheath first flow path 31. Moreover, a leading end of the aspiration section 12 formed as a nozzle is fitted to the more upstream end of the second flow path 32. The aspiration section 12 is a section that aspirates the liquid sample 70 in from a sample holder 60 holding the liquid sample 70 using a first pump 41, described later. A first valve 51 that is a three-way valve is provided partway along the second flow path 32. A third flow path 33 is connected to the second flow path 32 via the first valve 51. The sheath fluid 80 is supplied from the second pump 42 into the third flow path 33. In the present exemplary embodiment, plunger pumps are employed for both the first pump 41 and the second pump 42, enabling the sheath fluid 80 to also be aspirated from the first flow path 31 and the third flow path 33. Note that the second pump 42 may employ a pump, such as a tube pump, that only has fluid delivery functionality and does not have a aspiration function.

The sheath fluid supply section 13 is a tank to store the sheath fluid 80 for supply to the flow cell 20 through the first pump 41 and the second pump 42. A sheath fluid supply path 35 that is tubing interconnected to the first pump 41 and the second pump 42 extends from the sheath fluid supply section 13. On the sheath fluid supply path 35 there is a first sheath fluid valve 54 provided between the sheath fluid supply section 13 and the first pump 41, and there is a second sheath fluid valve 55 provided between the sheath fluid supply section 13 and the second pump 42. The first sheath fluid valve 54 and the second sheath fluid valve 55 are both one-way open-shut valves.

Note that in the present exemplary embodiment, the sides of the first flow path 31, the second flow path 32, and the third flow path 33 toward the flow cell 20 are defined as being downstream sides, and the opposite sides thereof are defined as being upstream sides.

On the second flow path 32 there is also a second valve 52 that is a three-way valve provided between the first valve 51 and the flow cell 20. Furthermore, there is also a third valve 53 that is a three-way valve provided partway along the first flow path 31. The second valve 52 and the third valve 53 are interconnected by a fourth flow path 34.

The first flow path 31, the second flow path 32, and the third flow path 33, and the fourth flow path 34, and also the sheath fluid supply path 35 and the waste liquid path 36 are all configured by tubing of a flexible and soft material (for example, TEFLON (registered trademark) tube).

From out of the three flow paths joining at the first valve 51, the third flow path 33 side is referred to as a branch 1A, the downstream side of the second flow path 32 is referred to as a branch 1B, and the upstream side of the second flow path 32 is referred to as a branch 1C. Moreover, from out of the three flow paths joining at the second valve 52, the upstream side of the second flow path 32 is referred to as a branch 2A, the downstream side of the second flow path 32 is referred to as a branch 2B, and the fourth flow path 34 is referred to as a branch 2C. Furthermore, from out of the three flow paths joining at the third valve 53, the upstream side of the first flow path 31 is referred to as a branch 3A, the downstream side of the first flow path 31 is referred to as a branch 3B, and the fourth flow path 34 is referred to as a branch 3C.

Flow Cell 20

Figure 2:
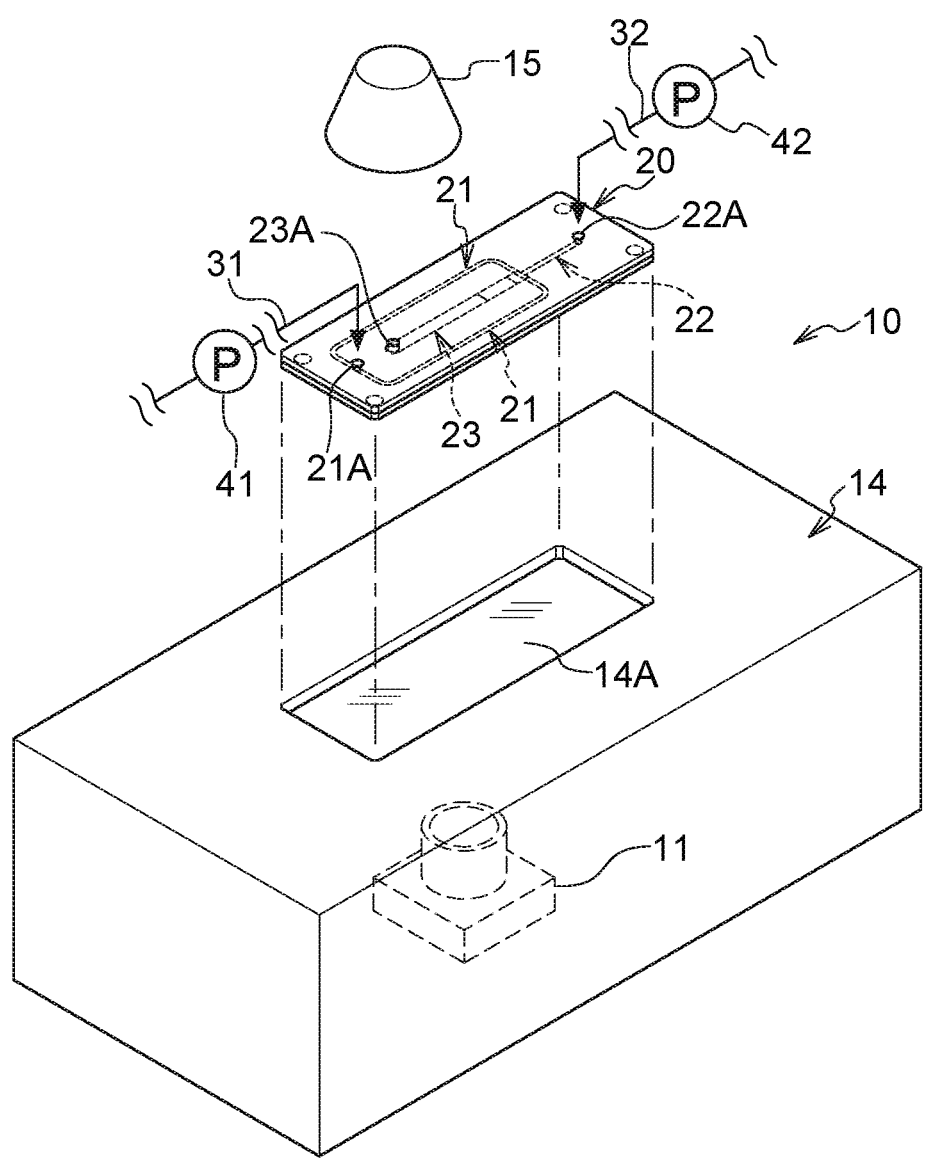
FIG. 2 is a perspective view schematically illustrating a positional relationship between a flow cell and a measurement device in an analysis device of the exemplary embodiment.

As illustrated in FIG. 2, the flow cell 20 is mounted to a recess 14A in a case 14 appropriate for the analysis device 10. A light source 15 and the measurement device 11 are installed at positions facing each other across the confluent flow path 23 of the flow cell 20, and more specifically at positions facing each other across the taper section 23C, provided with the inclined face of the first inner wall 23E, to the flat section 23D (see FIG. 7). The light source 15 shines a light beam onto the liquid sample 70 flowing through the confluent flow path 23. The measurement device 11 measures the liquid sample 70 flowing together with the sheath fluid 80 in the confluent flow path 23. Namely, the measurement device 11 measures the liquid sample 70 flowing through flow path at a section of the confluent flow path 23 facing toward the measurement device 11 across the bottom face 23Y. The liquid sample 70 flows in this flow path section while being pressed by the sheath fluid 80 flowing along the first inner wall 23E. Thus in the present exemplary embodiment, this flow path section corresponds to the measurement flow path provided downstream of the taper section 23C. Note that measurements referred to here include detecting a particular component of the liquid sample 70 in a quantitative or qualitative manner with an optical measurement device (such as a spectrophotometer) as the measurement device 11, and also observing and imaging images using a camera or the like as a different example of the measurement device 11. Moreover, the measurement device 11 is placed in close proximity to the bottom face 23Y that is the wall face opposing the top face 23X that is the wall face provided with the first inner wall 23E.

Figure 3:
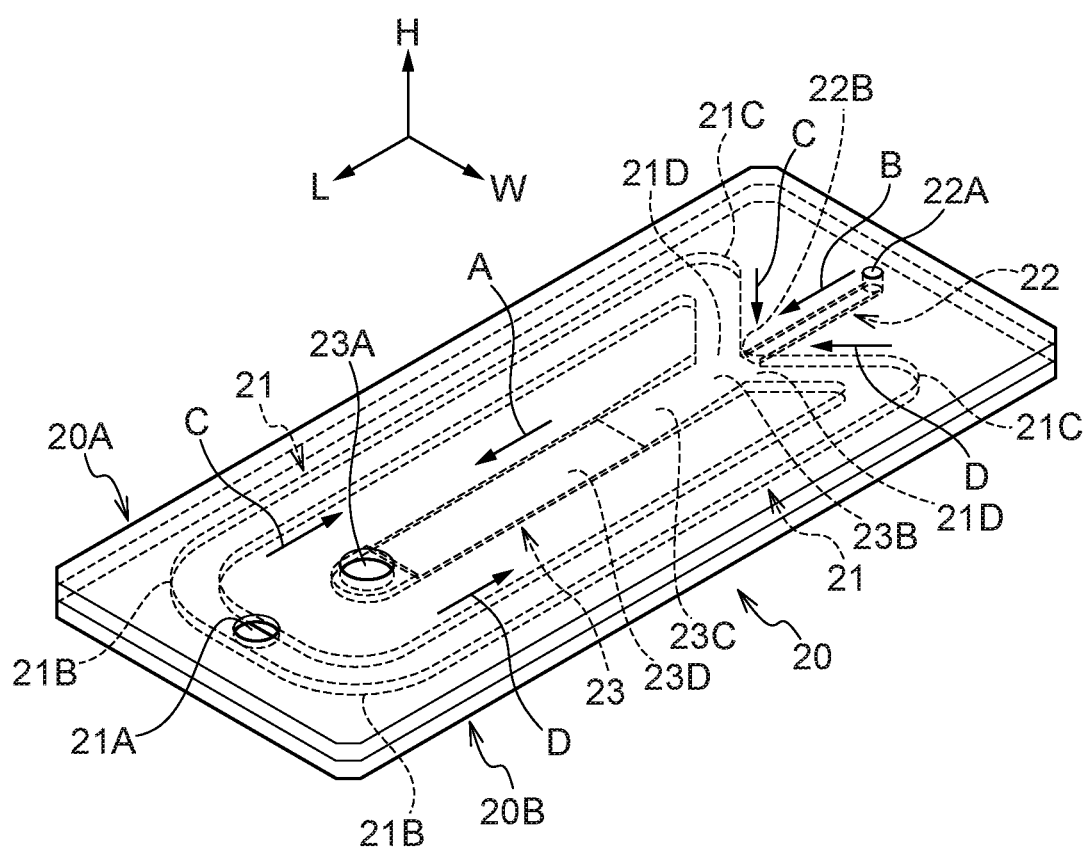
FIG. 3 is perspective view illustrating a flow cell according to the exemplary embodiment.
Figure 4:
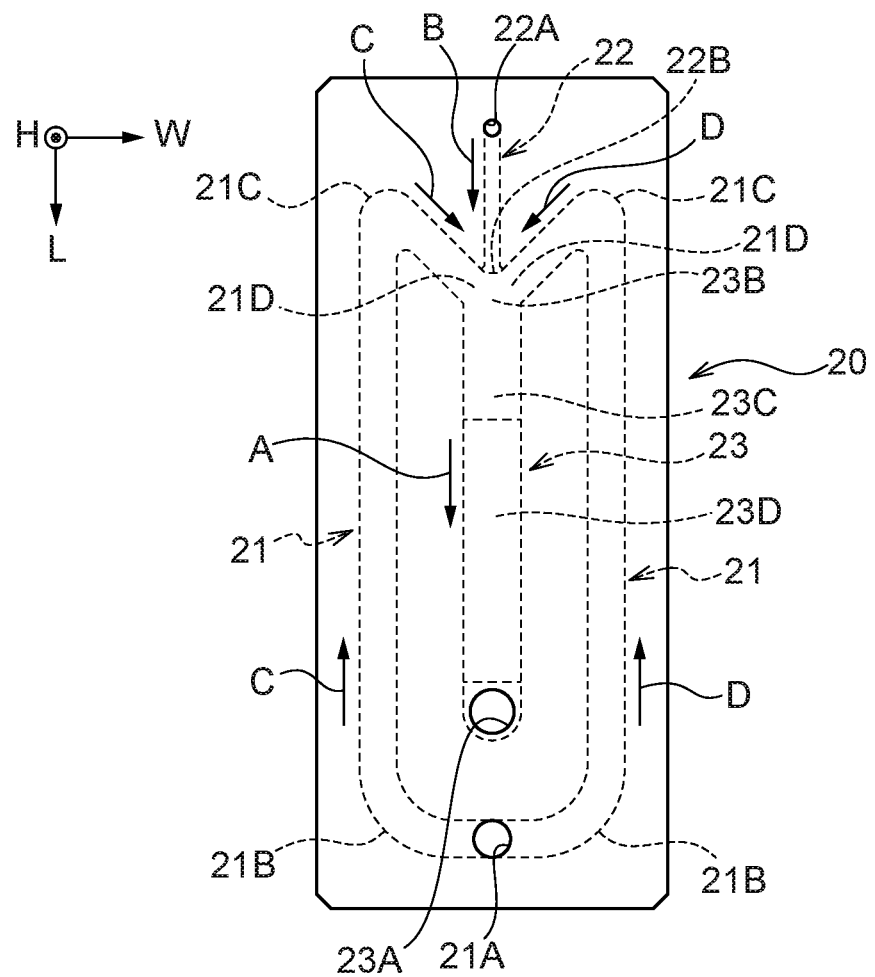
FIG. 4 is a plan view illustrating a flow cell according to the exemplary embodiment.
Figure 5:
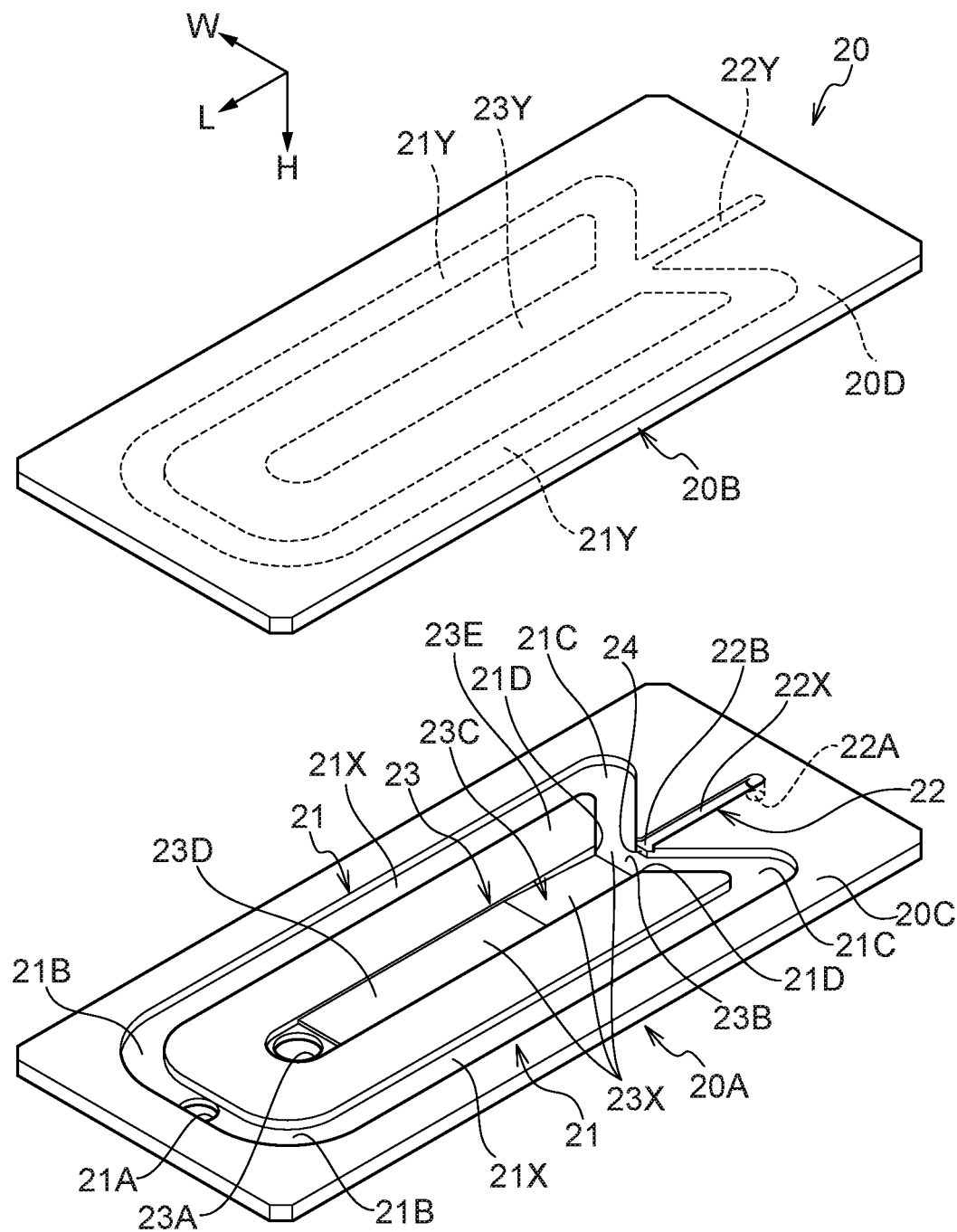
FIG. 5 is an exploded perspective view illustrating a flow cell according to the exemplary embodiment.
Figure 6:
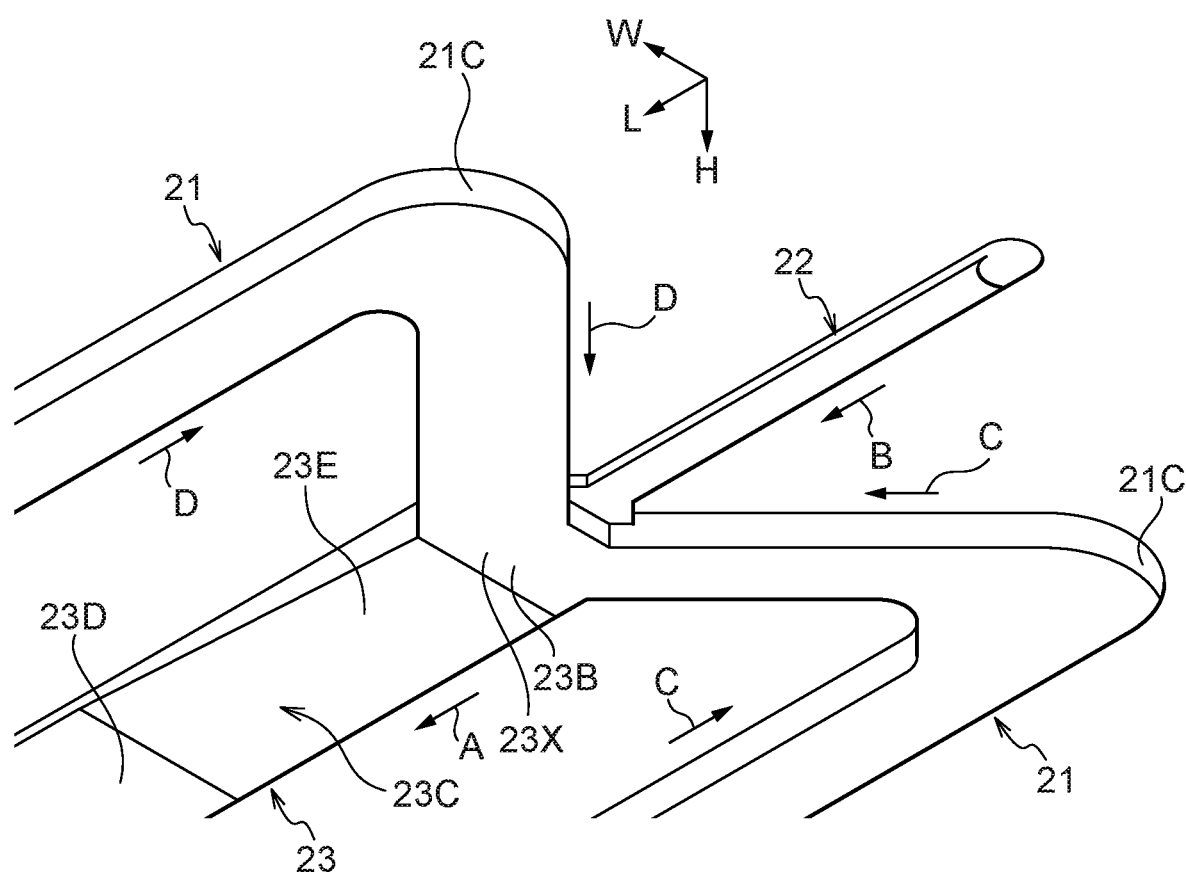
FIG. 6 is an enlarged perspective view illustrating a vicinity of a confluent section of a liquid sample and a sheath fluid in a flow cell according to the exemplary embodiment.

FIG. 3 is a perspective view of the flow cell 20 of the present exemplary embodiment, and FIG. 4 is a plan view of the flow cell 20. FIG. 5 is an exploded perspective view of the flow cell 20. FIG. 6 is an enlarged perspective view illustrating a state arising in the vicinity of the confluent section 23B, described later, of the flow cell 20. Note that as appropriate, the arrow H indicates a height direction of the flow cell 20 and an arrow W indicates a width direction of the flow cell 20. Moreover, in the drawings, the arrow L indicates a length direction of the flow cell 20 orthogonal to both the height direction and the width direction (the arrow L indicates a downstream side in a direction of flow of the sheath fluid 80 and the liquid sample 70 in the flow path after joining). In order to facilitate understanding of the configuration of the flow cell 20, FIG. 5 and FIG. 6 are illustrated in a state in which the height direction (H direction), i.e. the up-down direction, is reversed from that in FIG. 1 and FIG. 2.

The flow cell 20 of the present exemplary embodiment may, for example, be employed in urine formed element tests in which a urine sample serving as an example of the liquid sample 70 caused to flow together with the sheath fluid 80, any formed elements in the urine sample are imaged with the measurement device 11, and the shape etc. of the formed elements in the obtained images is analyzed. Although in the present exemplary embodiment a urine sample is employed for a liquid as an example of the liquid sample 70 and urine formed element tests are performed thereon, any liquid sample such a body fluid like blood may be employed as the liquid sample 70.

As illustrated in FIG. 3 to FIG. 5, the flow cell 20 is formed as a substantially rectangular shaped plate member. In the present exemplary embodiment, the flow cell 20 is configured by sticking an upper plate member 20A and a lower plate member 20B together in a face-to-face contact state. The flow cell 20 is equipped with the confluent flow path 23 through which the liquid sample 70 and the sheath fluid 80 join together and flow, and the sample flow path 22 through which the liquid sample 70 flows provided on a line extending along the length direction of the confluent flow path 23 at the upstream side (opposite side to direction L) in the flow direction in the confluent flow path 23 indicated by arrow A (see FIG. 5). Moreover, the flow cell 20 is also equipped with two sheath fluid flow paths 21 through which the sheath fluid 80 flows that are arranged so as to intersect with the length direction of the confluent flow path 23 at the upstream side in the flow direction (arrow A direction) in the confluent flow path 23.

The confluent flow path 23, the liquid sample flow path 22, and the two sheath fluid flow paths 21 are provided in the upper plate member 20A (see FIG. 5). Note that in FIG. 5 the positional relationships of the two sheath fluid flow paths 21 are reversed to those of FIG. 1 and FIG. 2 since the up and down directions of the flow cell 20 are reversed with respect to those of FIG. 1 and FIG. 2. In the present exemplary embodiment, the confluent flow path 23, the liquid sample flow path 22, and the two sheath fluid flow paths 21 are formed by machining grooves in a bottom face 20C (a face facing upwards in FIG. 5) of the upper plate member 20A (see FIG. 5). Note that a portion at the bottom of the grooves forming the sheath fluid flow paths 21 in FIG. 5 configures a top face 21X of the respective sheath fluid flow paths 21. Moreover, a portion at the bottom of the groove forming the liquid sample flow path 22 configures a top face 22X of the liquid sample flow path 22. Furthermore, a portion at the bottom of the groove forming the confluent flow path 23 configures a top face 23X of the confluent flow path 23. The lower plate member 20B is a plate member equipped with substantially parallel flat faces on the top and bottom, with no flow path or the like formed therein (see FIG. 5). However, the upper face 20D thereof (a face facing downward in the drawings) configures a bottom face 21Y of the sheath fluid flow path 21, a bottom face 22Y of the liquid sample flow path 22, and a bottom face 23Y of the confluent flow path 23.

The liquid sample flow path 22 is arranged in a substantially straight line along the length direction of the flow cell 20, and the liquid sample 70 flows along the sample flow path 22 in the arrow B direction. In the present exemplary embodiment the sample flow path 22 has a substantially rectangular shaped cross-sectional profile taken along a direction orthogonal to the length direction thereof. An in-take port 18A is formed at an upstream side end in the flow direction (arrow B direction) of the sample flow path 22, and the liquid sample 70 is supplied into the in-take port 18A. The second flow path 32 (see FIG. 1) for supplying the liquid sample 70 is connected to the sample port 22A of the sample flow path 22. The sample flow path 22 is configured so that the liquid sample 70 supplied from the sample port 22A flows in the direction toward the confluent flow path 23.

The two sheath fluid flow paths 21 are substantially U-shaped flow paths arranged with the widthwise length of each of the substantially U-shapes along the length direction of the flow cell 20 in plan view, and with the open side of each of the substantially U-shapes facing each other in the width direction (W direction) of the flow cell 20. The two sheath fluid flow paths 21 oppose each other in the width direction (W direction) of the flow cell 20, across the confluent flow path 23 interposed therebetween. In the present exemplary embodiment each of the sheath fluid flow paths 21 has a substantially rectangular shaped cross-sectional profile taken along a direction orthogonal to the length direction of the sheath fluid flow path 21.

The two sheath fluid flow paths 21 are configured so that the sheath fluid 80 flows respectively in the arrow C direction and the arrow D direction. The sheath fluid port 21A is formed at the upstream side end in the flow direction (arrow C direction and arrow D direction) of the two sheath fluid flow paths 21, and the sheath fluid 80 is supplied into the sheath fluid port 21A. In other words, the sheath fluid flow path 21 is configured so that the sheath fluid 80 supplied from the sheath fluid port 21A flows toward the upstream side of the confluent flow path 23. There are two bent portions 21B, 21C formed respectively to each of the two sheath fluid flow paths 21 partway along the flow direction therein. The bent portion 21B of each of the sheath fluid flow paths 21 at the upstream side in the flow direction is bent to a substantially orthogonal direction, and a corner portion of the bent portion is bent so as to form a rounded shape. Bent portions 21C further to the downstream side than the two bent portions 21B (the side just before the confluent section 23B) are each bent to an acute angle direction, and a corner portion of the bent portion is bent so as to form a rounded shape.

The confluent section 23B is provided at the upstream side end in the flow direction (arrow A direction) of the confluent flow path 23, and the liquid sample 70 flowing from the sample flow path 22 and the sheath fluid 80 flowing from the two sheath fluid flow paths 21 join together in the confluent section 23B (see FIG. 6). Namely, the confluent section 23B is a portion of the confluent flow path 23.

Figure 7:
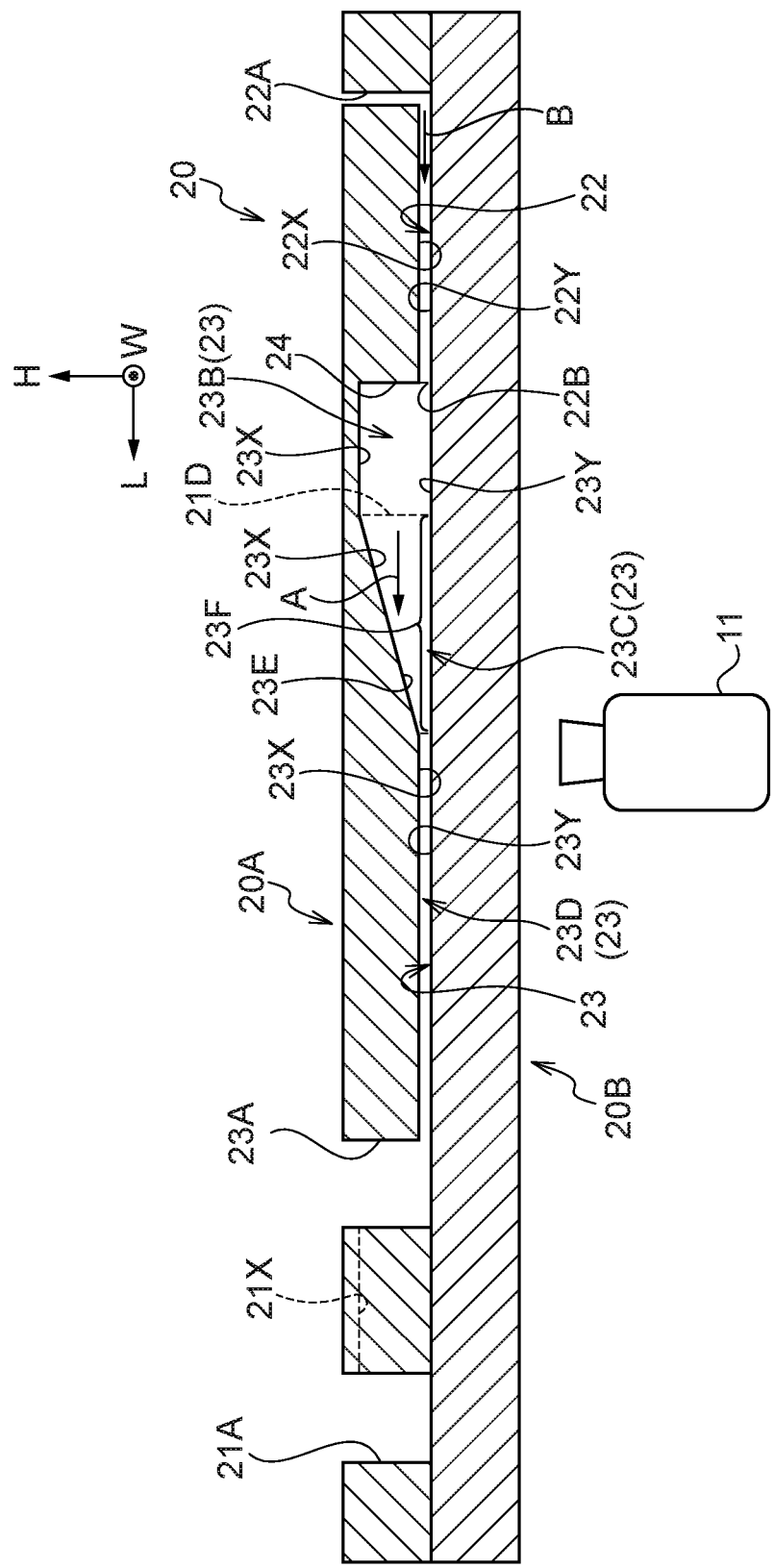
FIG. 7 is a cross-section illustrating a flow cell according to the exemplary embodiment.

As illustrated in FIG. 7, a sample inflow port 22B is provided at a downstream side end in the flow direction (arrow B direction) of the sample flow path 22, and the sample inflow port 22B opens onto an end face 24 at the upstream side in the flow direction (arrow A direction) of the confluent flow path 23 (see FIG. 1 to FIG. 3). The sample inflow port 22B is formed at one depth direction side of the end face 24 of the confluent flow path 23 (in the present exemplary embodiment, at a lower portion thereof in the opposite direction to the H direction). More specifically, the confluent flow path 23 is equipped with the bottom face 23Y and the top face 23X that are wall faces opposing each other along the depth direction. The sample flow path 22 is provided so as to run along an extension direction of the bottom face 23Y in the confluent section 23B of the confluent flow path 23, with this bottom face 23Y being the wall face opposing the wall face provided with the first inner wall 23E in the taper section 23C. The bottom face 22Y of the sample flow path 22 is connected to and in the same plane as the bottom face 23Y of the confluent flow path 23. This thereby achieves a configuration in which the liquid sample 70 in the sample flow path 22 flows into the confluent section 23B through the sample inflow port 22B. In other words, the sample flow path 22 is configured so as to cause the liquid sample 70 in the confluent section 23B to flow into the confluent section 23B along the bottom face 23Y of the confluent flow path 23. Namely, in the present exemplary embodiment, the second pump 42 serves as a sample delivery device 42 (see FIG. 1) so as to deliver the sample along an inner wall opposing the first inner wall 23E.

Sheath fluid inflow ports 21D are provided at each downstream side end in the flow direction (arrow C direction and arrow D direction) of the sheath fluid flow paths 21, and the sheath fluid inflow ports 21D open onto side portions at both upstream sides in the flow direction (arrow A direction) of the confluent flow path 23 (see FIG. 1 to FIG. 3). In plan view the sheath fluid inflow ports 21D of the sheath fluid flow path 21 are formed at positions intersecting with the end face 24 of the confluent flow path 23. In the present exemplary embodiment, the downstream end portions of the sheath fluid flow paths 21 are configured so as to be connected to the confluent section 23B so as to form an acute angle with respect to the length direction of the confluent flow path 23. Moreover, the sheath fluid flow paths 21 are provided so as to run along extension directions of the top face 23X in the confluent flow path 23, with the wall face 23X being the wall face provided with the first inner wall 23E in the taper section 23C from out of the opposing wall faces. In the present exemplary embodiment, the sheath fluid inflow ports 21D of the sheath fluid flow paths 21 are provided in a range of the confluent section 23B from the bottom face 23Y to the top face 23X, so that lower portions of the sheath fluid inflow ports 21D overlap with the range where the sample inflow port 22B is provided as viewed in cross-section taken along the depth direction of the confluent flow path 23 (see FIG. 5). This thereby achieves a configuration in which the sheath fluid 80 of the sheath fluid flow paths 21 flows into the confluent section 23B of the confluent flow path 23 from the sheath fluid inflow ports 21D. In other words, a configuration is achieved in which the sheath fluid flow paths 21 causes the sheath fluid 80 to flow into the confluent section 23B from a direction so that the sheath fluid 80 presses the liquid sample 70 so as to flow against the bottom face 23Y. Namely, in the present exemplary embodiment, the first pump 41 serves as a sheath fluid delivery device 41 (see FIG. 1) so as to deliver sheath fluid along the first inner wall 23E.

Figure 12:
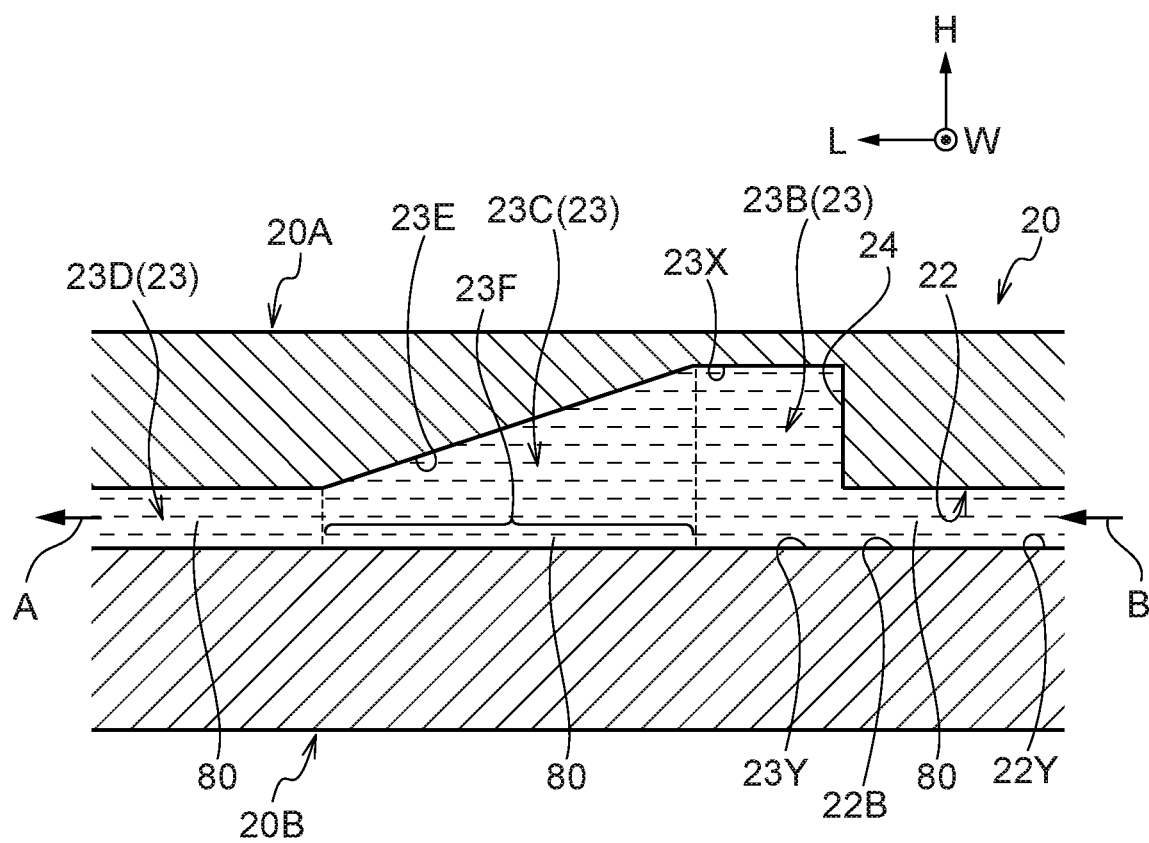
FIGS. 12 and 13 are cross-sections illustrating a vicinity of a confluent section of a flow cell.

In the flow cell 20 of the present exemplary embodiment, the length direction of the sample flow path 22 is arranged along an extension line along the length direction of the confluent flow path 23. In the present exemplary embodiment, the confluent flow path 23 has a substantially rectangular shaped cross-sectional profile taken along a direction orthogonal to the length direction of the confluent flow path 23. The width and depth dimensions of the confluent flow path 23 are both respectively larger than the width and depth dimensions of the sample flow path 22. The sample flow path 22 is connected to a width direction central portion of the confluent section 23B of the confluent flow path 23, and connected to a depth direction lower portion of the confluent section 23B of the confluent flow path 23 (see FIG. 7). Moreover, in the present exemplary embodiment, so as not to waste the liquid sample 70, the sheath fluid 80 first flows into the confluent section 23B of the confluent flow path 23 from the sheath fluid flow path 21 (see FIG. 12). Then, the liquid sample 70 flows from the sample flow path 22 (see FIG. 14).

At the downstream side in the flow direction (arrow A direction) of the confluent section 23B of the confluent flow path 23, the taper section 23C is provided on an upper wall portion of the confluent flow path 23, with the top face 23X gradually approaching the bottom face 23Y on progression downstream (see FIG. 6 and FIG. 7). The taper section 23C include the first inner wall 23E and the second inner wall 23F opposing the first inner wall 23E. In the present exemplary embodiment, the first inner wall 23E is arranged in upper direction of the second inner wall 23F. In other words, in the present exemplary embodiment, the taper section 23C is formed with a profile having a gradually shorter distance between the bottom face 23Y and the top face 23X that are the opposing wall faces. Namely, this portion of the top face 23X of the taper section 23C is configured by the first inner wall 23E that is inclined in a direction approaching the opposing wall face on progression from upstream to downstream. In other words, the first inner wall 23E is inclined to the second inner wall 23F so that a distance between the first inner wall 23E and the second inner wall 23F at a downstream side of the taper section is shorter than a distance between the first inner wall 23E and the second inner wall 23F at an upstream side of the taper section. In the present exemplary embodiment, the taper section 23C is provided at a position adjacent to the confluent section 23B of the confluent flow path 23. The taper section 23C has an angle of inclination with respect to the in-plane direction of the flow cell 20 (the plane direction of the bottom face 23Y in the present exemplary embodiment) of, for example, from 2° to 8°.

At the downstream side in the flow direction (arrow A direction) of the taper section 23C of the confluent flow path 23, the flat section 23D is formed so as to maintain the height at the downstream end of the taper section 23C. In other words, the distance between the top face 23X and the bottom face 23Y that are the opposing wall faces in the flat section 23D is shorter than the distance between the top face 23X and the bottom face 23Y that are the opposing wall faces in the confluent section 23B. The taper section 23C is configured so as to join the confluent section 23B and the flat section 23D.

In the flow cell 20, the liquid sample 70 is configured so as to flow along the bottom face 23Y due to the bottom face 23Y of the confluent flow path 23 being arranged so as to be connected to and in the same plane as the bottom face 22Y of the sample flow path 22. Furthermore, a configuration is achieved in which the sheath fluid 80 that joins the confluent section 23B from the sheath fluid flow paths 21 flows so as to press the liquid sample 70 against the bottom face 23Y (see FIG. 15). Note that as long as the sample flow path 22 is provided so that the liquid sample 70 flows along bottom face 23Y in the confluent section 23B, the taper section 23C, and the flat section 23D, the respective bottom faces 22Y, 23Y of the sample flow path 22, the confluent section 23B, the taper section 23C, and the flat section 23D do not necessarily need to be in the same plane as each other. For example, curved planes may be adopted therefor, and there may be angles respectively provided in the bottom faces 22Y, 23Y.

A camera serving as the measurement device 11 to image the liquid sample 70 is arranged outside the flow cell 20 at a position facing toward the flat section 23D (see FIG. 7). Namely, the flat section 23D corresponds to the measurement flow path. Furthermore, the measurement device 11 is arranged at a position where the liquid sample 70 flows in contact with the bottom face 23Y. The cross-sectional area of the sheath fluid flow path 21 is larger than the cross-sectional area of the sample flow path 22.

As illustrated in FIG. 3 to FIG. 5, a waste liquid port 23A is formed at a downstream side end in the flow direction (arrow A direction) of the confluent flow path 23 to discharge a waste liquid 75 arising from mixing of the liquid sample 70 and the sheath fluid 80 together. The waste liquid path 36 is connected to the waste liquid port 23A so that the waste liquid 75 passing through the waste liquid path from the waste liquid port 23A is discharged to an external section, not illustrated in the drawings.

The flow cell 20 is preferably formed from a transparent material, for example, a material having a transparency to visible light of not less than 90%, such as, for example, glass, or a synthetic resin such as polymethyl methacrylate resin, a cyclo olefin polymer resin, a polydimethylsiloxane resin, a polypropylene resin, or the like. The confluent flow path 23, the sample flow path 22, and the two sheath fluid flow paths 21 etc. are formed in the upper plate member 20A by laser machining or the like. The flow cell 20 is formed by sticking the upper plate member 20A and the lower plate member 20B together. In the present exemplary embodiment, for example, the upper plate member 20A and the lower plate member 20B are stuck together by thermocompression bonding.

Functional Blocks

Figure 8:
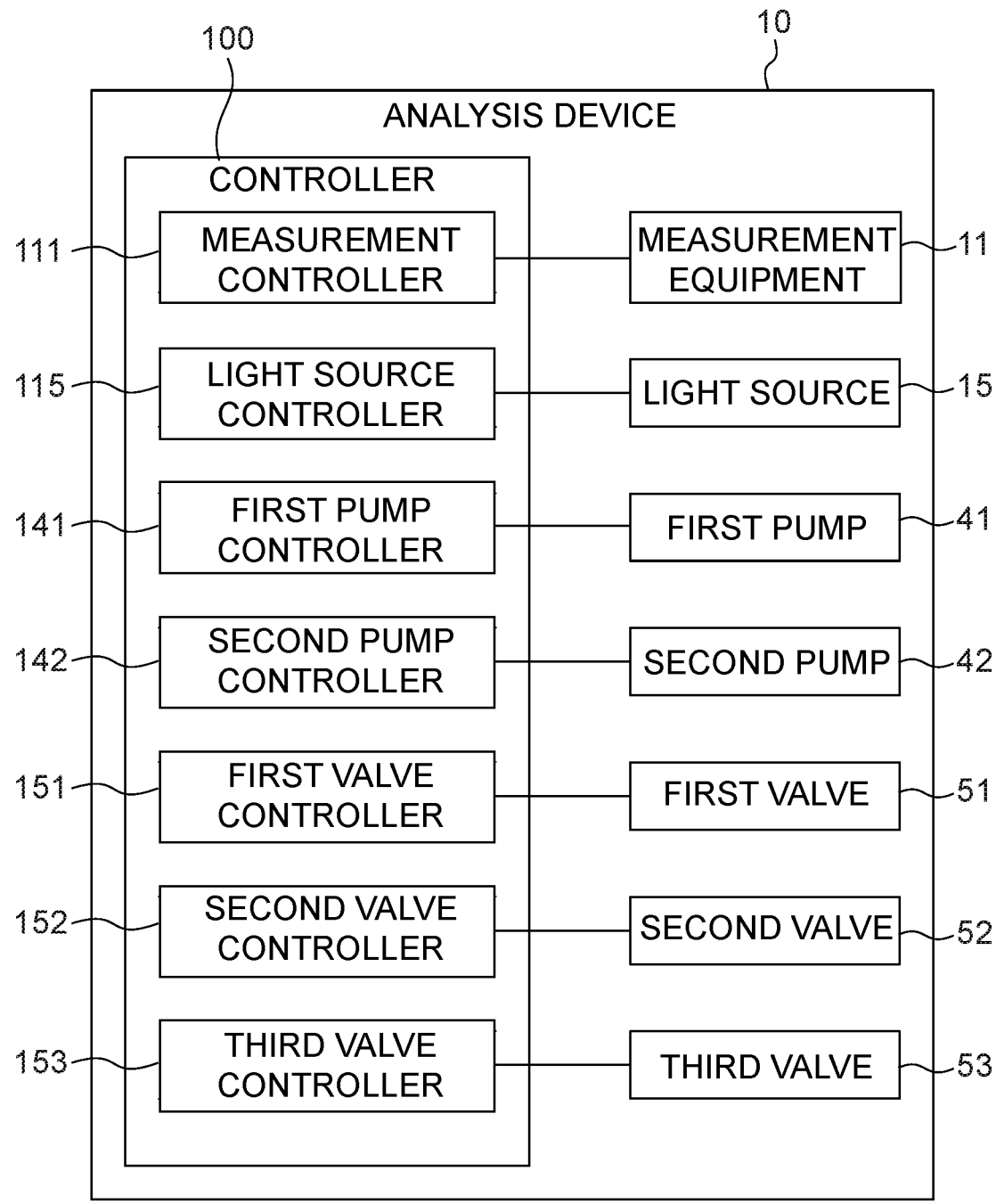
FIG. 8 is a functional block diagram of an analysis device of the exemplary embodiment.

FIG. 8 is a functional block diagram of the analysis device 10. A controller 100 controls each section of the analysis device 10. Due having the hardware configuration described later, the controller 100 functions as a measurement controller 111 to control the measurement device 11, a light source controller 115 to control the light source 15, a first pump controller 141 to control supply and aspiration of liquid by the first pump 41, a second pump controller 142 to control supply and aspiration of liquid by the second pump 42, a first valve controller 151 to control flow path switching in the first valve 51, a second valve controller 152 to control flow path switching in the second valve 52, and a third valve controller 153 to control flow path switching in the third valve 53.

Figure 9:
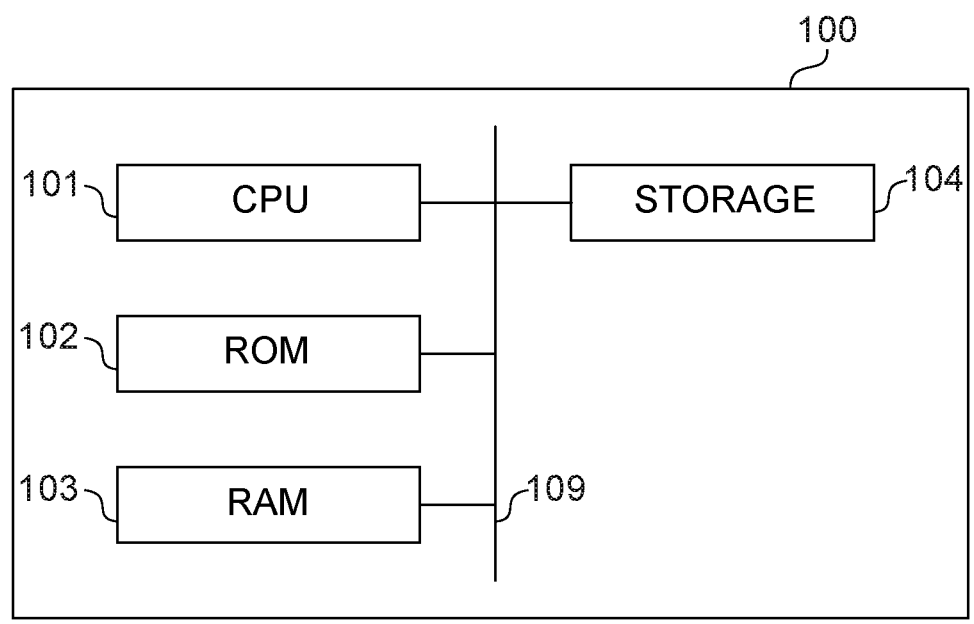
FIG. 9 is a block diagram illustrating a hardware configuration of a controller.

As illustrated by the hardware configuration of FIG. 9, the controller 100 includes a central processing unit (CPU) 101, read only memory (ROM) 102, random access memory (RAM) 103, and storage 104. These configuration elements are all connected together via a bus 109 so as to be capable of communicating with each other.

The CPU 101 is a central processing unit, and controls each of the sections by executing various programs. Namely, the CPU 101 reads a program from the ROM 102 or the storage 104, and executes the program using the RAM 103 as workspace. The CPU 101 performs control of the configuration elements listed above and various computation processing according to the programs recorded in the ROM 102 or the storage 104.

The ROM 102 stores various programs and various data. The RAM 103 serves as a workspace for temporarily storing programs and data. The storage 104 is configured by a hard disk drive (HDD), solid state drive (SSD), or flash memory, and is stored with various programs including an operating system, and with various data. In the present exemplary embodiment, a program and various data related to measurement and determination is stored in the ROM 102 or the storage 104. Measurement data may also be saved in the storage 104.

Due to the CPU 101 with the hardware configuration described above executing the program, the controller 100 functions as the measurement controller 111, the light source controller 115, the first pump controller 141, the second pump controller 142, the first valve controller 151, the second valve controller 152, and the third valve controller 153 of the analysis device 10, as illustrated in FIG. 8. These functions are described more precisely later.

Analysis Device 10 Operation

Figure 10:
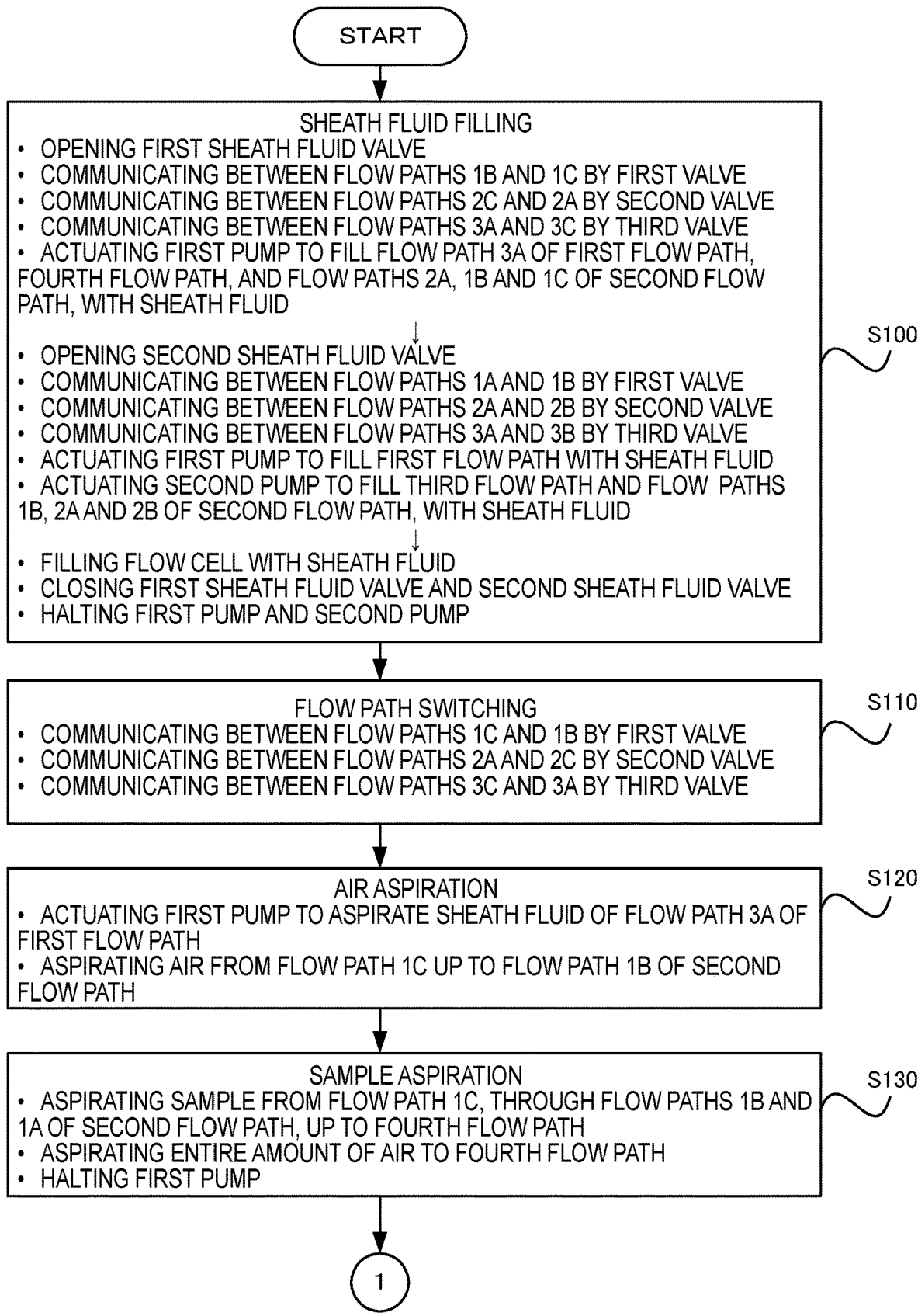
FIGS. 10 and 11 are flowcharts illustrating operation of an analysis device of the exemplary embodiment.
Figure 11:
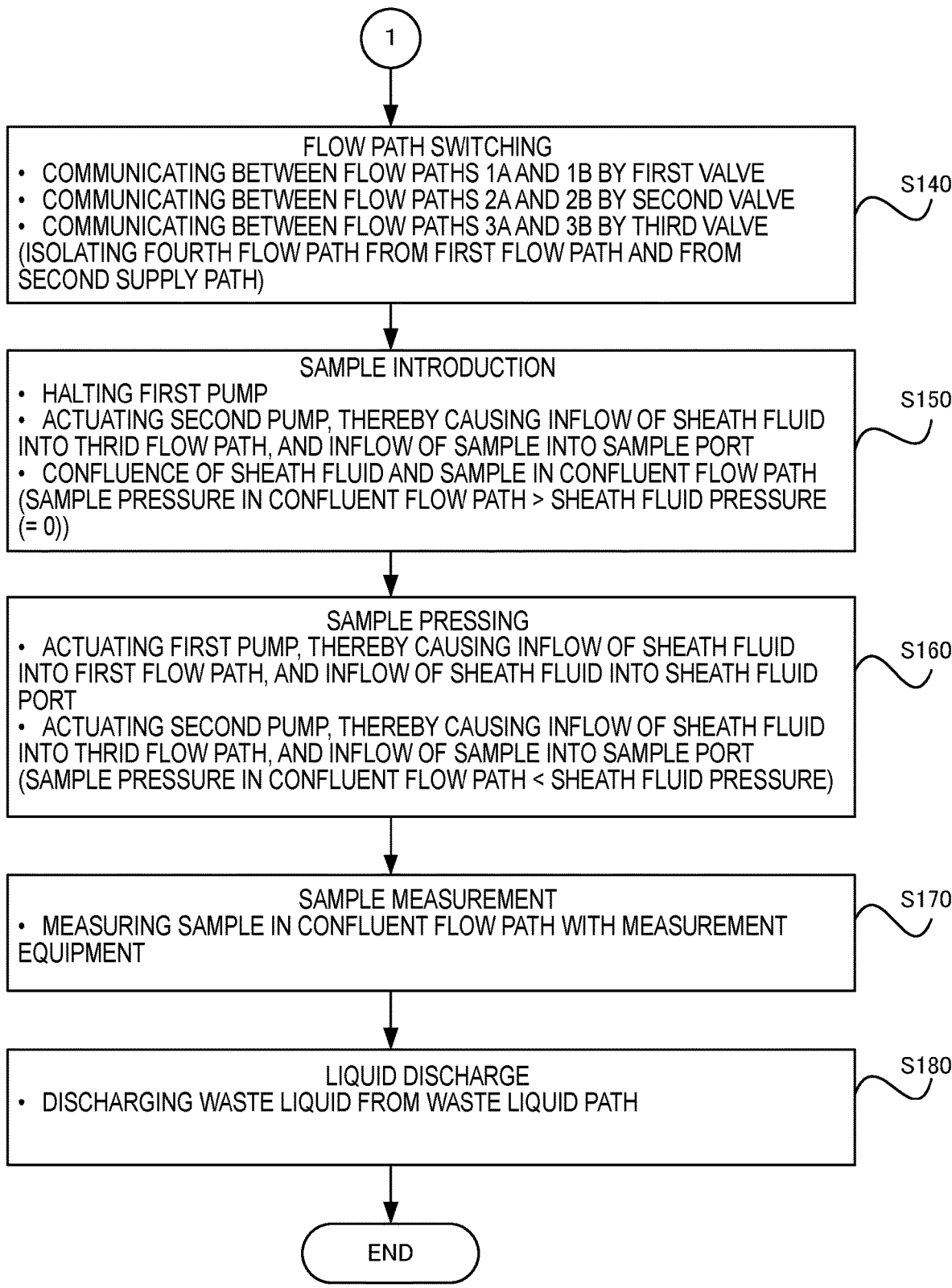

The operation of the analysis device 10 of the present exemplary embodiment will now be described, with reference to FIG. 10 to FIG. 15. Note that FIG. 10 and FIG. 11 are flowcharts illustrating operation of an analysis device of the present exemplary embodiment. Each part of the analysis device is as illustrated in FIG. 1. Note that arrows appended in the vicinity of the lines in FIG. 13 indicate the direction of flow of liquid (or gas), and the directions colored black at each of the valves indicate the direction of flow path thereat.

Prior to starting to use the analysis device 10, each of the lines of the analysis device 10 is filled with the sheath fluid 80 in a sheath fluid filling step S100 of FIG. 10. First the first sheath fluid valve 54 is opened. Then the first valve controller 151 communicates the flow paths of the branch 1B and the branch 1C at the first valve 51, the second valve controller 152 communicates the flow paths of the branch 2A and the branch 2C at the second valve 52, and the third valve controller 153 communicates the flow paths of the branch 3A and the branch 3C at the third valve 53.

From this state, the first pump controller 141 actuates the first pump 41, and the sheath fluid 80 is supplied into the first flow path 31. The sheath fluid 80 that is supplied into the first pump 41 from the sheath fluid supply section 13 via the first sheath fluid valve 54 thereby flows from the first pump 41 through the third valve 53, the second valve 52, and the first valve 51, and reaches the aspiration section 12 where it is discharged from the leading end thereof. Namely, the branch 3A of the first flow path 31, the fourth flow path 34, and the branch 2A, branch 1B, and the branch 1C of the second flow path 32 are thereby filled with the sheath fluid 80 from the first pump 41.

Next, the second sheath fluid valve 55 is opened together with the first sheath fluid valve 54. Then the first valve controller 151 communicates the flow paths of the branch 1A and the branch 1B at the first valve 51, the second valve controller 152 communicates the flow paths of the branch 2A and the branch 2B at the second valve 52, and the third valve controller 153 communicates the flow paths of the branch 3A and the branch 3B at the third valve 53.

From this state, the first pump controller 141 then actuates the first pump 41, and the sheath fluid 80 is supplied into the first flow path 31. Thereby, the sheath fluid 80 supplied to the first pump 41 from the sheath fluid supply section 13 via the first sheath fluid valve 54 flows from the first pump 41 through the third valve 53 and reaches the flow cell 20. Namely, the first flow path 31 is completely filled with the sheath fluid 80 from the first pump 41, through the third valve 53, to the flow cell 20.

At the same time, the second pump controller 142 actuates the second pump 42 and supplies the sheath fluid 80 into the third flow path 33. Thereby the sheath fluid 80 supplied to the second pump 42 from the sheath fluid supply section 13 via the second sheath fluid valve 55 flows from the second pump 42, through the first valve 51 and the second valve 52, and reaches the flow cell 20. Namely, the third flow path 33, and the branch 1B, the branch 2A, and the branch 2B of the second flow path 32 are all filled with the sheath fluid 80 from the second pump 42.

Furthermore, in the flow cell 20, the sheath fluid 80 from the first flow path 31 also fills the two branches of the sheath fluid flow paths 21 through the sheath fluid port 21A. Moreover, the sheath fluid 80 from the second flow path 32 fills the sample flow path 22 through the sample port 22A. The sheath fluid 80 from both directions joins in the confluent flow path 23, fills the confluent flow path 23, and then after the waste liquid path 36 is filled through the waste liquid port 23A, is discharged to an external section, not illustrated in the drawings.

Each of the lines in the analysis device 10 is thereby filled with the sheath fluid 80. Then, in the flow cell 20, in a state in which the sample flow path 22, the confluent section 23B, the taper section 23C, and the flat section 23D are filled with the sheath fluid 80, as illustrated by the cross-section of FIG. 12, the first pump controller 141 controls to halt the actuation of the first pump 41. At the same time, the second pump controller 142 controls to halt the actuation of the second pump 42. In this state, the fluid delivery pressure of the sheath fluid 80 is substantially nil, or extremely low, in the confluent flow path 23.

Then, at a flow path switching step S110 of FIG. 10, the first valve controller 151 communicates the flow paths of the branch 1B and the branch 1C at the first valve 51, the second valve controller 152 communicates the flow paths of the branch 2A and the branch 2C at the second valve 52, and third valve controller 153 communicates the flow paths of the branch 3A and the branch 3C at the third valve 53.

From this state, at an air aspiration step S120 of FIG. 10, the first pump controller 141 actuates the first pump 41, imparts a negative pressure to the first flow path 31, and the sheath fluid 80 is aspirated from the branch 3A of the first flow path 31. Air 90 is thereby aspirated from the aspiration section 12. The aspirated air 90 reaches the branch 1B from the branch 1C of the second flow path 32.

When the aspiration section 12 is immersed in the liquid sample 70 held in the sample holder 60 while maintaining this operational state and continuing to impart a negative pressure to the first flow path 31, at a sample aspiration step S130 of FIG. 10, the liquid sample 70 is aspirated from the aspiration section 12, passes from the branch 1C of the second flow path 32 through the branch 1B and the branch 2A, and reaches the branch 2C of the fourth flow path 34. The entire amount of the aspirated air 90 passes the second valve 52, and reaches the fourth flow path 34. In this state, the first pump controller 141 halts actuation of the first pump 41, and a negative pressure halts being imparted to the first flow path 31. This thereby seals the entire amount of the aspirated air 90 in the fourth flow path 34.

Then, at a flow path switching step S140 of FIG. 11, the first valve controller 151 communicates the flow paths of the branch 1A and the branch 1B at the first valve 51, the second valve controller 152 communicates the flow paths of the branch 2A and the branch 2B at the second valve 52, and the third valve controller 153 communicates the flow paths of the branch 3A and the branch 3B at the third valve 53.

In this state, at a sample introduction step S150 of FIG. 11, the second pump controller 142 actuates the second pump 42 while the first pump 41 remains halted, a positive pressure is imparted to the third flow path 33, and supply of the sheath fluid 80 into the third flow path 33 is resumed. The sheath fluid 80 is thereby caused to flow from the second pump 42 through the first valve 51 and the second valve 52, so as to extrude the liquid sample 70 in the second flow path 32 so as to flow into the flow cell 20. At this point, the first pump 41 is not being actuated, and so the inflow of the sheath fluid 80 to the flow cell 20 from the first flow path 31 is halted.

Figure 13:
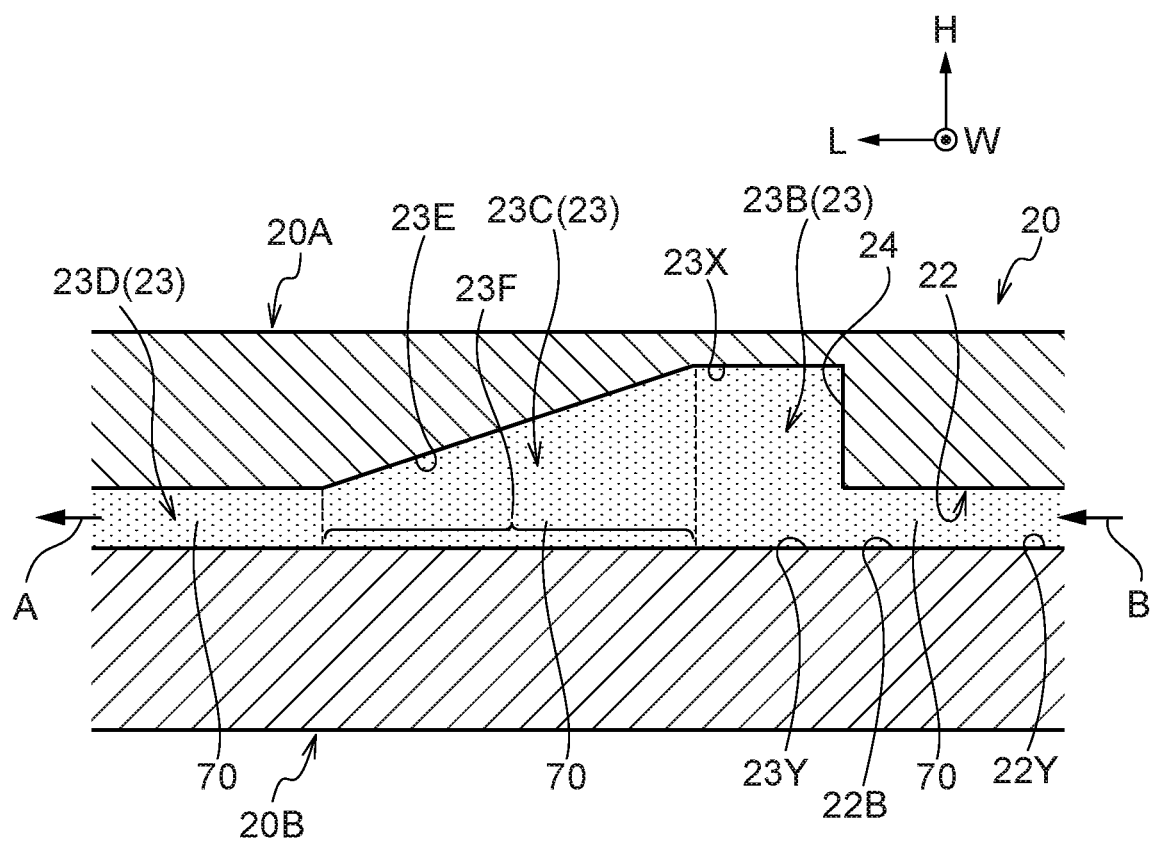

In this state, at the confluent section 23B of the flow cell 20, as illustrated in the cross-section of FIG. 13, the liquid sample 70 flowing from the sample flow path 22 extrudes the sheath fluid 80 downstream, fills the confluent section 23B, and reaches the flat section 23D. The fluid delivery pressure of the liquid sample 70 in the confluent flow path 23 at this point is obviously greater than the fluid delivery pressure of the sheath fluid 80 in the confluent flow path 23. Namely, the controller 100 controls so that the fluid delivery pressure of the liquid sample 70 inside the confluent flow path 23 as delivered by the second pump 42 under control from the second pump controller 142 is greater than the fluid delivery pressure inside the confluent flow path 23 of the sheath fluid 80 as delivered by the now halted first pump 41. Note that although in the present exemplary embodiment the first pump 41 is halted and the sheath fluid 80 is not delivered into the confluent flow path 23 until the liquid sample 70 reaches the flat section 23D, the present disclosure is not limited thereto. Namely, the controller 100 may be configured to actuate the first pump 41 and deliver the sheath fluid 80 in such a manner that the fluid delivery pressure thereof is less than the fluid delivery pressure of the liquid sample 70 inside the confluent flow path 23 as delivered by the second pump 42 under control from the second pump controller 142, so as to be less than the fluid delivery pressure inside the confluent flow path 23 of the liquid sample 70 as delivered by the second pump 42.

Figure 14:
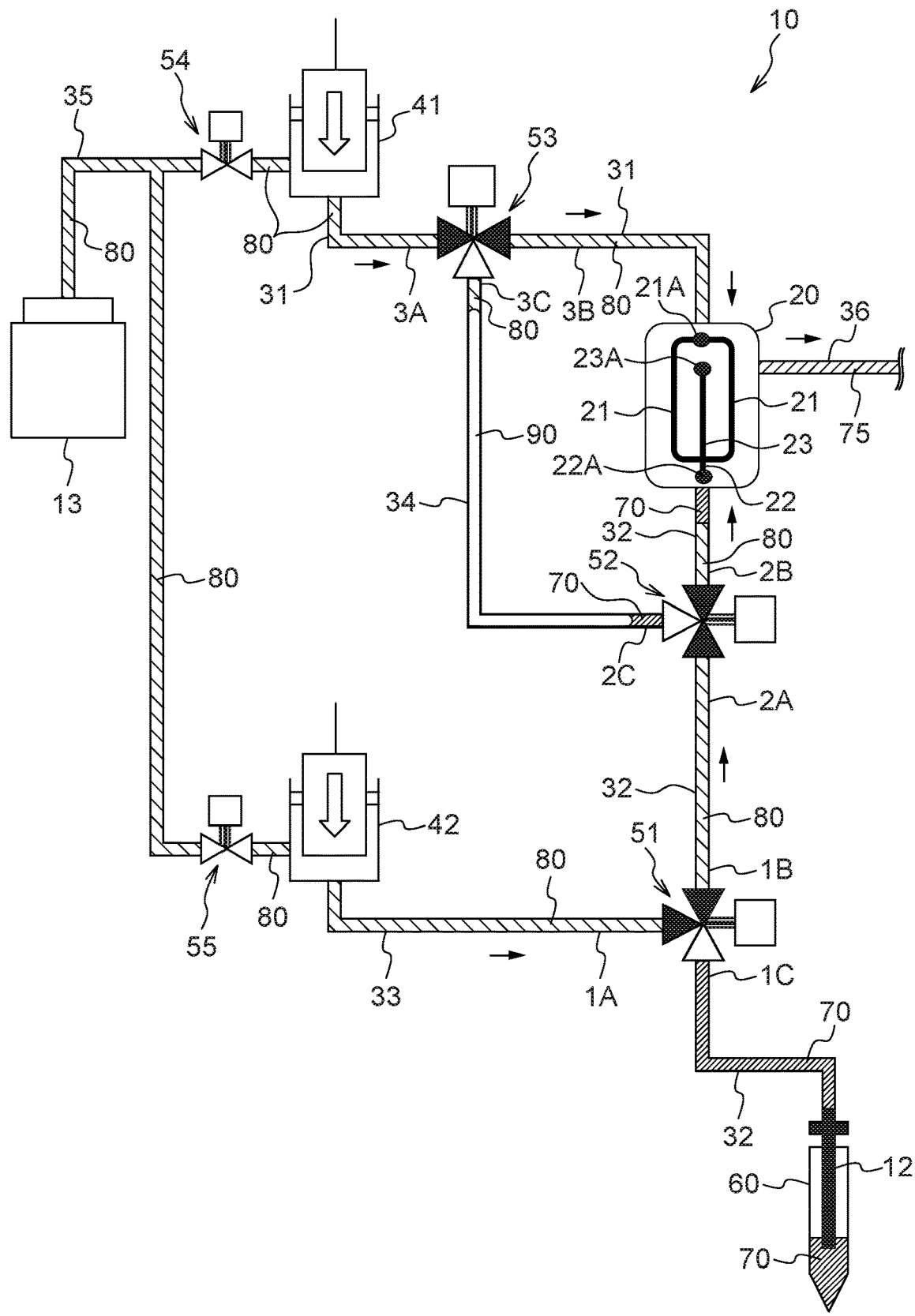
FIG. 14 is a schematic diagram illustrating operation of an analysis device of the exemplary embodiment.

Then, at a sample pressing step S160 of FIG. 11, as illustrated in FIG. 14, the first pump controller 141 re-actuates the first pump 41 while the second pump controller 142 is still actuating the second pump 42, and inflow of the sheath fluid 80 to the flow cell 20 from the first flow path 31 is restarted. Namely, the sheath fluid 80 of the first flow path 31 flowing from the sheath fluid port 21A to the flow cell 20 first branches into the two sheath fluid flow paths 21, and then joins the liquid sample 70 in the confluent flow path 23.

Figure 15:
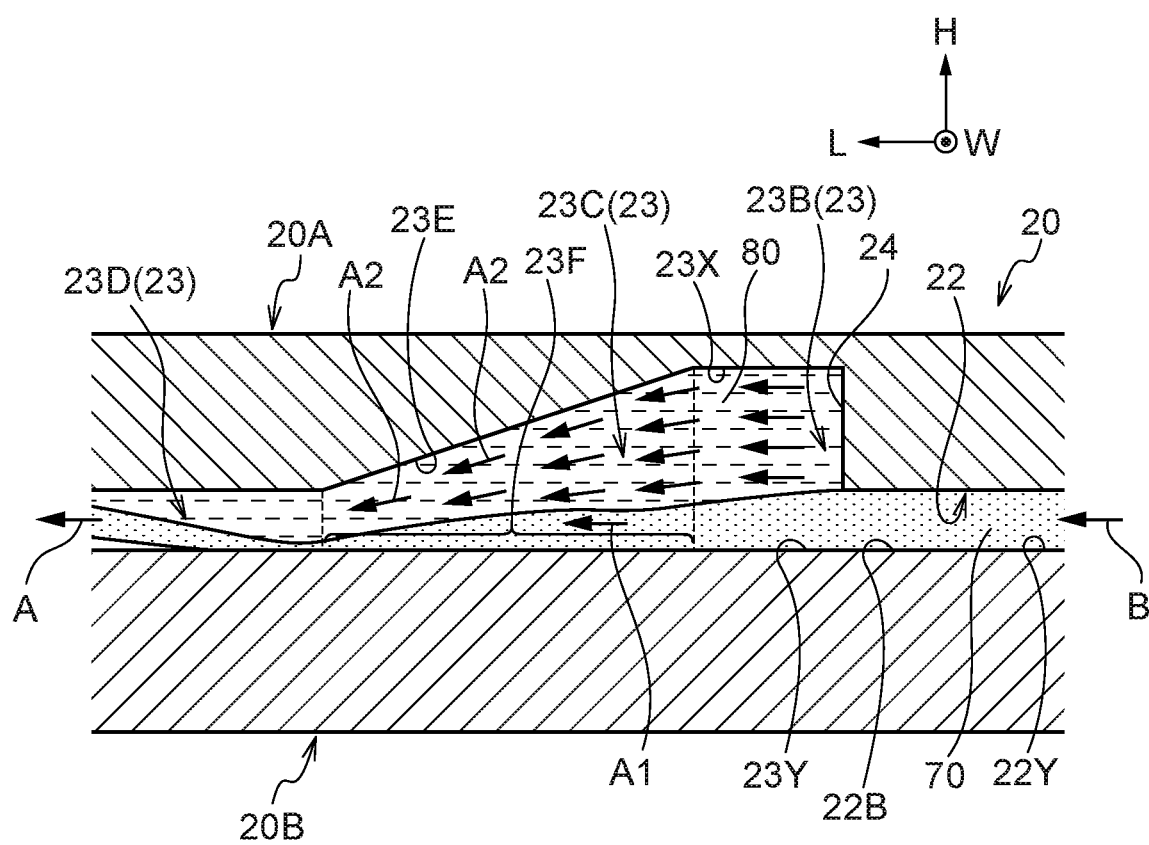
FIG. 15 is a cross-section illustrating a vicinity of a confluent section of a flow cell.

In this state, the liquid sample 70 and the sheath fluid 80 join together at the confluent section 23B of the flow cell 20, however, as illustrated in the cross-section of FIG. 15, the sheath fluid 80 of the sheath fluid flow path 21 flows along the top face 23X at the upper side of the liquid sample 70 flowing along the bottom faces 22Y, 23Y, and so mixing between the liquid sample 70 and the sheath fluid 80 is suppressed. When this occurs, controller 100 controls the fluid delivery pressure of the first pump 41 using the first pump controller 141 and at the same time controls the fluid delivery pressure of the second pump 42 by the second pump controller 142 so that the fluid delivery pressure of the sheath fluid 80 in the confluent flow path 23 is greater than the fluid delivery pressure of the liquid sample 70 in the confluent flow path 23. Namely, the pressure the first pump 41 delivers the sheath fluid into the confluent flow path 23 is controlled by the controller 100 so as to be greater than the pressure the second pump 42 delivers the liquid sample 70 into the confluent flow path 23.

The liquid sample 70 flowing from the sample flow path 22 flows in the direction of arrow A1 along the bottom face 23Y of the confluent flow path 23 due to the sample flow path 22 being provided so as to run along the extension direction of the bottom face 23Y of the confluent section 23B. Moreover, the sheath fluid 80 introduced from the sheath fluid flow path 21 flows into the confluent section 23B along the top face 23X of the confluent flow path 23 due to the sheath fluid flow paths 21 being provided so as to run along extension directions of the top face 23X that is the wall face provided with the first inner wall 23E. The taper section 23C is accordingly provided in which the top face 23X of the confluent flow path 23 gradually approaches the bottom face 23Y on progression downstream. Thereby, as illustrated in FIG. 15, in the confluent flow path 23, the sheath fluid 80 flowing into the confluent section 23B from the sheath fluid flow paths 21 flows along the first inner wall 23E of the taper section 23C, and flows along the direction of arrow A2 so as to press the liquid sample 70 against the bottom face 23Y of the confluent flow path 23. Thus, as illustrated in FIG. 15, in the taper section 23C of the confluent flow path 23, the liquid sample 70 is spread out into a flattened planar shape along the bottom face 23Y due to the liquid sample 70 being pressed from above by the sheath fluid 80, so that the thickness of the liquid sample 70 gradually gets thinner and the width gradually gets wider. At this point the liquid sample 70 flows in contact with the bottom face 23Y. Thus the liquid sample 70 flows along the bottom face at an upstream section of the flat section 23D of the confluent flow path 23, in a state in which the thickness of the liquid sample 70 is thinner and the width wider. The thickness of the liquid sample 70 at this point is, for example, from approximately 5 μm to approximately 30 mm. Namely, the measurement device 11 is disposed as illustrated in FIG. 7 at a position from the taper section 23C to the flat section 23D where the thickness of the liquid sample 70 is at its thinnest. Moreover, the light source 15 is disposed at a position facing toward the measurement device 11 across the flow cell 20.

At a sample measurement step S170 of FIG. 11, the liquid sample 70 pressed by the sheath fluid 80 in this manner is measured by the measurement device 11 controlled by the measurement controller 111 by being illuminated by the light source 15 having light intensity adjusted by the light source controller 115.

Thus due to the liquid sample 70 flowing in contact with the bottom face 23Y, the sheath fluid 80 is not interposed between the measurement device 11 and the liquid sample 70, enabling the liquid sample 70 to be measured without being affected by the sheath fluid 80. Moreover, the liquid sample 70 is spread out along the bottom face 23Y in a flattened planar shape, with a thickness that gets gradually thinner, and this is advantageous in a case in which an imaging device is employed as the measurement device 11 to observe the shape and size of formed elements contained in the liquid sample 70.

Note that the waste liquid 75 arising from mixing between the liquid sample 70 and the sheath fluid 80 in the confluent flow path 23 is, at a waste liquid discharge step S180 of FIG. 11, discharged from the waste liquid path 36 to an external section, not illustrated in the drawings, through the waste liquid port 23A.

The flow cell 20 of the present exemplary embodiment is configured so that the flow rate of the liquid sample 70 and the sheath fluid 80 of the sheath fluid flow path 21 is controlled. The ratio of flow rates of the liquid sample 70 to the sheath fluid 80 is set so as to be from 1:20 to 1:40. The width and thickness of the liquid sample 70 flowing in the confluent flow path 23 is controlled by controlling the ratio of flow rates between the liquid sample 70 and the sheath fluid 80. Controlling the flow rates is, for example, preferably achieved by controlling the flow rate of the sheath fluid 80 to not more than 3%, and by controlling the flow rate of the liquid sample 70 to not more than 50%.

INDUSTRIAL APPLICABILITY

The present disclosure is applicable to a fluid delivery method for a liquid sample to a flow cell, and to a sample analysis device employing such a method.

What is claimed is:
1. A fluid delivery method for delivering a liquid sample to a flow cell including a taper section that includes a first inner wall and a second inner wall opposing the first inner wall, the first inner wall being inclined to the second inner wall so that a distance between the first inner wall and the second inner wall at a downstream side of the taper section is shorter than a distance between the first inner wall and the second inner wall at an upstream side of the taper section,
   a sample flow path provided upstream of the taper section and formed with a first bottom face connected to and in the same plane as the second inner wall,
   a sheath fluid flow path provided upstream of the taper section and formed with a top face connected to the first inner wall, and
   a measurement flow path provided downstream of the taper section and formed with a second bottom face connected to the second inner wall,
   the fluid delivery method comprising:
       sample introduction by delivering the liquid sample into the sample flow path along the first bottom face until the liquid sample reaches the measurement flow path; and
       subsequent sample pressing by delivering the sheath fluid into the sheath fluid flow path after the liquid sample reaches the measurement flow path, whereby the liquid sample and the sheath fluid flow on the second bottom face so that the second bottom face, the liquid sample and the sheath fluid are arranged in this order.

2. The fluid delivery method of claim 1, wherein, in the sample introduction, the delivery of the sheath fluid to the taper section is halted.

3. The fluid delivery method of claim 2, wherein the sample introduction is performed after the measurement flow path is filled with the sheath fluid.

4. The fluid delivery method of claim 3, further comprising measurement of the liquid sample flowing in the measurement flow path after the sample pressing.

5. The fluid delivery method of claim 4, wherein the liquid sample is a body fluid.

6. The fluid delivery method of claim 5, wherein the body fluid is urine.

7. An analysis device, comprising:
a flow cell including a taper section that includes a first inner wall and a second inner wall opposing the first inner wall, the first inner wall being inclined to the second inner wall so that a distance between the first inner wall and the second inner wall at a downstream side of the taper section is shorter than a distance between the first inner wall and the second inner wall at an upstream side of the taper section, a sample flow path provided upstream of the taper section and formed with a first bottom face connected to and in the same plane as the second inner wall, a sheath fluid flow path provided upstream of the taper section and formed with a top face connected to the first inner wall, and a measurement flow path provided downstream of the taper section and formed with a second bottom face connected to the second inner wall;
a sheath fluid delivery device configured to deliver the sheath fluid into the sheath fluid flow path;
a sample delivery device configured to deliver the liquid sample into the sample flow path;
a measurement device configured to measure the liquid sample flowing in the measurement flow path; and
a controller configured to control the sample delivery device so as to deliver the liquid sample into the sample flow path along the first bottom face until the liquid sample reaches the measurement flow path, and to control the sheath fluid delivery device so as to subsequently deliver the sheath fluid into the sheath fluid flow path after the liquid sample reaches the measurement flow path, whereby the liquid sample and the sheath fluid flow on the second bottom face so that the second bottom face, the liquid sample and the sheath fluid are arranged in this order.

8. The analysis device of claim 7, wherein the controller is configured to control the sample delivery device so as to deliver the liquid sample into the taper section until the liquid sample is detected by the measurement device, and to control the sheath fluid delivery device so as to deliver the sheath fluid into the taper section after the liquid sample is detected by the measurement device.

* * * * *